United States Patent
Dischert et al.

(10) Patent No.: US 11,814,663 B2
(45) Date of Patent: Nov. 14, 2023

(54) MICROORGANISMS WITH IMPROVED 1,3-PROPANEDIOL AND BUTYRIC ACID PRODUCTION

(71) Applicant: METABOLIC EXPLORER, Saint Beauzire (FR)

(72) Inventors: Wanda Dischert, Vic-le-Comte (FR); Céline Raynaud, Saint Beauzire (FR); Laurence Dumon-Seignovert, Pont du Chateau (FR); Nadège Dumoulin, Gerzat (FR)

(73) Assignee: METABOLIC EXPLORER, Saint Beauzire (FR)

( * ) Notice: Subject to any disclaimer, the term of this patent is extended or adjusted under 35 U.S.C. 154(b) by 215 days.

(21) Appl. No.: 17/267,347

(22) PCT Filed: Aug. 9, 2019

(86) PCT No.: PCT/EP2019/071392
§ 371 (c)(1),
(2) Date: Feb. 9, 2021

(87) PCT Pub. No.: WO2020/030775
PCT Pub. Date: Feb. 13, 2020

(65) Prior Publication Data
US 2021/0254108 A1 Aug. 19, 2021

(30) Foreign Application Priority Data
Aug. 10, 2018 (EP) ..................... 18306099

(51) Int. Cl.
| C12P 7/52 | (2006.01) |
| C07K 14/33 | (2006.01) |
| C12N 9/02 | (2006.01) |
| C12N 9/12 | (2006.01) |
| C12P 7/18 | (2006.01) |
| C12N 1/20 | (2006.01) |

(52) U.S. Cl.
CPC ............... *C12P 7/52* (2013.01); *C07K 14/33* (2013.01); *C12N 1/20* (2013.01); *C12N 9/0067* (2013.01); *C12N 9/1205* (2013.01); *C12P 7/18* (2013.01); *C12Y 112/07002* (2013.01); *C12Y 207/0103* (2013.01)

(58) Field of Classification Search
CPC ........... C12P 7/52; C12N 1/20; C12N 9/0067; C07K 14/33
See application file for complete search history.

(56) References Cited

U.S. PATENT DOCUMENTS

| 2010/0028965 A1 | 2/2010 | Liu et al. |
| 2017/0022446 A1 | 1/2017 | Nouaille et al. |
| 2017/0240869 A1* | 8/2017 | Soucaille ................ C12P 7/065 |

FOREIGN PATENT DOCUMENTS

| EP | 0350355 A1 | 1/1990 |
| JP | 2006-512907 A | 4/2006 |
| WO | WO 02/077183 A2 | 10/2002 |
| WO | WO 2006/128381 A1 | 12/2006 |
| WO | WO 2008/040387 A1 | 4/2008 |
| WO | WO 2009/013160 A2 | 1/2009 |
| WO | WO 2009/068110 A1 | 6/2009 |
| WO | WO 2010/037843 A1 | 4/2010 |
| WO | WO 2010/128070 A2 | 11/2010 |
| WO | WO 2011/042434 A1 | 4/2011 |
| WO | WO 2012/062832 A1 | 5/2012 |
| WO | WO-2012062832 A1 * | 5/2012 | ............... C12N 1/32 |
| WO | WO 2013/050760 A2 | 4/2013 |
| WO | WO 2017/013335 A1 | 1/2017 |

OTHER PUBLICATIONS

González-Pajuelo, María, et al. "Microbial conversion of glycerol to 1, 3-propanediol: physiological comparison of a natural producer, Clostridium butyricum VPI 3266, and an engineered strain, Clostridium acetobutylicum DG1 (pSPD5)." Applied and environmental microbiology 72.1 (2006): 96-101. (Year: 2006).*

Tang, Weng Lin, and Huimin Zhao. "Industrial biotechnology: tools and applications." Biotechnology Journal: Healthcare Nutrition Technology 4.12 (2009): 1725-1739. (Year: 2009).*

González-Pajuelo, M., Meynial-Salles, I., Mendes, F., Soucaille, P., & Vasconcelos, I. (2006). Microbial conversion of glycerol to 1, 3-propanediol: physiological comparison of a natural producer, Clostridium butyricum VPI 3266, and an engineered strain, Clostridium acetobutylicum DG1 (pSPD5). A (Year: 2006).*

Tang, W. L., & Zhao, H. (2009). Industrial biotechnology: tools and applications. Biotechnology Journal: Healthcare Nutrition Technology, 4(12), 1725-1739. (Year: 2009).*

MicrobeWiki, "Clostridium acetobutylicum" retrieved from https://microbewiki.kenyon.edu/index.php/Clostridium_acetobutylicum on Mar. 6, 2023. Published 2013 (Year: 2013).*

Bantscheff et al., "Quantitative mas spectrometry in proteomics: a critical review," Anal Bioanal Chem, vol. 389, 2007, pp. 1017-1031.

Bertani, "I. The Mode of Phage Liberation By Lysogenic *Escherichia Coli*," Studies on Lysogenesis, vol. 62, 1951, pp. 293-300.

(Continued)

*Primary Examiner* — Robert J Yamasaki
*Assistant Examiner* — Trevor Kane
(74) *Attorney, Agent, or Firm* — Birch, Stewart, Kolasch & Birch, LLP

(57) ABSTRACT

The present invention concerns a new mutant strain of *Clostridium acetobutylicum* comprising attenuated glycerol kinase activity. In addition, the present invention concerns a consortium of *Clostridium* comprising at least said mutant strain and at least one other species of *Clostridium* chosen among *C. sporogenes* and *C. sphenoides*. As this modified strain may be adapted for growth and for the production of 1,3-propanediol in an appropriate culture medium with high glycerol content, the invention also relates to a method for the production of 1,3-propanediolandbutyric acid, by culturing at least this mutant strain in an appropriate culture medium.

19 Claims, No Drawings

Specification includes a Sequence Listing.

(56) References Cited

OTHER PUBLICATIONS

Burnette, "Western Blotting: Electrophoretic Transfer of Proteins from Sodium Dodecyl Sulfate-Polyacrylamide Gels to Unmodified Nitrocellulose and Radiographic Detection with Antibody and Radioiodinated Protein A," Analytical Biochemistry, vol. 112, 1981, pp. 195-203.

Cingolani et al., "A program for annotating and predicting the effects of single nucleotide polymorphisms, SnpEff: SNPs in the genome of *Drosophila melanogaster* strain w1118, iso-2; iso-3," Fly, vol. 6, Issue 2, 2012, pp. 80-92.

DePristo et al., "A framework for variation discovery and genotyping using next generation DNA sequencing data," Nat Genet., vol. 43, No. 5, May 2011, pp. 491-498 (20 pages total).

Engvall et al., "Enzyme-linked immunosorbent assay (ELISA) Quantitative assay of immunoglobulin G," Communications to the Editors, IMM, vol. 8, No. 9-1, pp. 871-874.

European Search Report for European Application No. 18306099, completed Jan. 17, 2019.

Gonzáles-Pajuelo et al., "Microbial Conversion of Glycerol to 1,3-Propanediol: Physiological Comparison of a Natural Producer, Clostridium butyricum VPI 3266 . . . ," Applied and Environmental Microbiology, vol. 72, No. 1, Jan. 2006, pp. 96-101.

González-Pajuelo et al., "Metabolic engineering of Clostridium acetobutylicum for the industrial production of 1,3-propanediol from glycerol," Metabolic Engineering, vol. 7, 2005 (published online Aug. 10, 2005), pp. 329-336.

International Search Report (Form PCT/ISA/210) for International Application No. PCT/EP2019/071392, dated Oct. 24, 2019.

McKenna et al., "The Genome Analysis Toolkit: A MapReduce framework for analyzing next-generation DNA sequencing data," Genome Research, vol. 20, 2010, pp. 1297-1303.

Nölling et al., "Genome Sequence and Comparative Analysis of the Solvent-Producing Bacterium Clostridium acetobutylicum," Journal of Bacteriology, vol. 183, No. 16, Aug. 2001, pp. 4823-4838.

Papanikolaou et al., "High production of 1,3-propanediol from industrial glycerol by a newly isolated Clostridium butylicum strain," Journal of Biotechnology, vol. 77, 2000, pp. 191-208.

Vasconcelos et al., "Regulation of Carbon and Electron Flow in Clostridium acetobutylicum Grown in Chemostat Culture at Neutral pH on Mixtures of Glucose and Glycerol," Journal of Bacteriology, vol. 176, No. 3, Mar. 1994, pp. 1443-1450.

* cited by examiner

SEQUENCE LISTING

```
<160> NUMBER OF SEQ ID NOS: 47

<210> SEQ ID NO 1
<211> LENGTH: 498
<212> TYPE: PRT
<213> ORGANISM: Clostridium acetobutylicum

<400> SEQUENCE: 1
```

Met Lys Lys Tyr Ile Ile Ala Leu Asp Gln Gly Thr Thr Ser Ser Arg
1               5                   10                  15

Ala Ile Ile Phe Asp His Glu Gln Asn Ile Leu Glu Ile Ser Gln Lys
            20                  25                  30

Glu Phe Thr Gln Ile Tyr Pro Ser Lys Gly Trp Val Glu His Asn Pro
        35                  40                  45

Leu Glu Ile Trp Ser Ser Gln Tyr Gly Val Leu Gln Glu Val Met Ala
    50                  55                  60

Lys Ala Asn Ile Thr Gln Glu Asn Ile Ala Ala Ile Gly Ile Thr Asn
65                  70                  75                  80

Gln Arg Glu Thr Thr Ile Val Trp Asp Lys Asn Thr Gly Glu Pro Val
                85                  90                  95

Tyr Asn Ala Ile Val Trp Gln Cys Arg Arg Thr Ala Asp Ile Val Glu

```
              100                 105                 110
Gly Leu Lys Arg Asp Lys Glu Phe Ser Asp Tyr Val Lys Glu Asn Thr
            115                 120                 125

Gly Leu Ile Leu Asp Ala Tyr Phe Ser Ala Thr Lys Ile Lys Trp Ile
            130                 135                 140

Leu Asp Asn Val Glu Gly Ala Arg Glu Lys Ala Lys Gly Glu Leu
145                 150                 155                 160

Leu Phe Gly Thr Val Asp Thr Trp Leu Val Trp Lys Leu Thr Asn Gly
                165                 170                 175

Lys Val His Val Thr Asp Tyr Thr Asn Ala Ser Arg Thr Met Leu Tyr
                180                 185                 190

Asn Ile Lys Glu Leu Lys Trp Asp Glu Arg Ile Leu Arg Lys Leu Asn
            195                 200                 205

Ile Pro Arg Ser Met Leu Pro Glu Val Lys Asn Ser Ser Glu Val Tyr
            210                 215                 220

Gly Tyr Thr Asn Leu Gly Gly Lys Gly Gly Ile Arg Val Pro Ile Ala
225                 230                 235                 240

Gly Met Ala Gly Asp Gln Gln Cys Ala Leu Phe Gly Gln Thr Cys Phe
                245                 250                 255

Glu Glu Gly Ser Val Lys Asn Thr Tyr Gly Thr Gly Cys Phe Leu Leu
                260                 265                 270

Met Asn Thr Gly Glu Asn Ile Ile Gln Ser Lys Asn Gly Leu Val Thr
                275                 280                 285

Thr Ile Ala Ile Gly Leu Glu Gly Lys Val Gln Tyr Ala Leu Glu Gly
            290                 295                 300

Ser Val Phe Val Gly Gly Ala Val Ile Gln Trp Ile Arg Asp Glu Leu
305                 310                 315                 320

Lys Leu Val Ser Asp Ala Ala Asp Thr Glu Tyr Phe Ala Lys Lys Val
                325                 330                 335

Asn Asp Asn Gly Gly Val Tyr Val Val Pro Ala Phe Thr Gly Leu Gly
                340                 345                 350

Ala Pro Tyr Trp Asp Met Tyr Ala Arg Gly Ala Ile Phe Gly Leu Thr
                355                 360                 365

Arg Gly Ala Asn Lys Asn His Ile Ile Arg Ala Ala Leu Glu Ala Ile
            370                 375                 380

Ala Tyr Gln Ser Arg Asp Leu Ile Asp Ala Met Lys Glu Asp Ser Gly
385                 390                 395                 400

Cys Glu Ile Thr Arg Ile Lys Val Asp Gly Gly Ala Ser Arg Asn Asn
                405                 410                 415

Leu Leu Met Gln Phe Gln Ala Asp Ile Thr Gly Thr Glu Val Val Arg
                420                 425                 430

Pro Ile Ile Thr Glu Thr Thr Ala Leu Gly Ala Ala Tyr Leu Ala Gly
                435                 440                 445

Leu Ala Val Gly Phe Trp Lys Ser Lys Glu Glu Ile Ala Glu Lys Trp
                450                 455                 460

Ser Val Ser Glu Val Tyr Thr Pro Asn Leu Asp Glu Asp Glu Lys Ile
465                 470                 475                 480

Arg Leu Tyr Asn Gly Trp Lys Arg Ala Val Glu Arg Val Gln Gly Trp
                485                 490                 495

Glu Glu

<210> SEQ ID NO 2
<211> LENGTH: 1497
```

```
<212> TYPE: DNA
<213> ORGANISM: Clostridium acetobutylicum

<400> SEQUENCE: 2
atgaagaaat atataatagc attagatcaa ggaactacaa gttcaagagc aataatattt      60
gaccatgaac aaaatatatt agaaattagt caaaaggaat ttactcaaat ctatccgagt     120
aaaggatggg ttgagcataa tcctttagag atatggtcaa gtcaatatgg agttttgcaa     180
gaagtaatgg caaaagctaa tataactcaa gaaatattg cagcaatagg aattactaat      240
caaagagaaa caacaattgt ttgggacaaa atactggag aacctgtgta taatgctatt      300
gtatggcagt gtagaagaac agcagatata gtggaaggac ttaagagaga taaagagttt     360
tcagattatg taaaagaaaa tacaggatta atattagatg catattttc agcaacaaaa      420
ataaagtgga tattagataa tgtagagggt gcaagagaaa aagctgaaaa aggtgaattg     480
ctatttggta cagttgatac ttggcttgta tggaagctaa caaatggcaa agtccatgta     540
accgattaca caaatgcatc tagaactatg ctttataata taaggaatt aaaatgggat      600
gaaagaattt taagaaaact taatattcca agatcaatgc taccagaagt taaaaattca     660
tccgaagttt atggatatac aaaccttgga ggtaaaggtg gtattagagt accaatagca     720
ggcatggcag gagatcaaca atgtgcatta tttggtcaaa cctgttttga agaaggtagt     780
gttaaaaata cttatggcac aggatgcttt ttacttatga atacaggaga aaatataatt     840
cagagtaaaa atggactagt aacgacaatt gcaattggat tagaagggaa agttcaatat     900
gcattagaag gttcagtgtt tgttgggggg gcagttattc agtggattag agatgaactt     960
aagttagtta gcgatgctgc ggatacagag tattttgcta aaaaagtgaa tgacaatggt    1020
ggagtatatg tggtaccagc atttactggt cttggagctc atattggga tatgtatgct    1080
agaggagcaa ttttttggtct gacaagaggc gcaaataaaa accatataat tagagcggca    1140
cttgaagcta ttgcatatca gtcaagagat cttatagatg caatgaaaga gattcgggga    1200
tgtgaaatta caagaattaa agttgatgga ggagctagta gaaataattt attaatgcag    1260
tttcaagcag acattacagg aacagaagtt gtaagaccta taataactga acaacagca     1320
cttggtgcag cttatttagc cggacttgct gtaggcttt ggaagtcaaa agaagaaatt    1380
gccgagaagt ggtctgtgag tgaggtgtat actccgaatt tagatgagga tgagaaaata    1440
agattatata acggttggaa gagagcagtt gaaagagttc agggctggga agaataa       1497

<210> SEQ ID NO 3
<211> LENGTH: 498
<212> TYPE: PRT
<213> ORGANISM: Clostridium acetobutylicum

<400> SEQUENCE: 3

Met Lys Lys Tyr Ile Ile Ala Leu Asp Gln Gly Thr Thr Ser Ser Arg
1               5                   10                  15

Ala Ile Ile Phe Asp His Glu Gln Asn Ile Leu Glu Ile Ser Gln Lys
            20                  25                  30

Glu Phe Thr Gln Ile Tyr Pro Ser Lys Gly Trp Val Glu His Asn Pro
        35                  40                  45

Leu Glu Ile Trp Ser Ser Gln Tyr Gly Val Leu Gln Glu Val Met Ala
    50                  55                  60

Lys Ala Asn Ile Thr Gln Glu Asn Ile Ala Ala Ile Gly Ile Thr Asn
65                  70                  75                  80

Gln Arg Glu Thr Thr Ile Val Trp Asp Lys Asn Thr Gly Glu Pro Val
```

```
                         85                  90                  95
Tyr Asn Ala Ile Val Trp Gln Cys Arg Arg Thr Ala Asp Ile Val Glu
                100                 105                 110
Gly Leu Lys Arg Asp Lys Glu Phe Ser Asp Tyr Val Lys Glu Asn Thr
                115                 120                 125
Gly Leu Ile Leu Asp Ala Tyr Phe Ser Ala Thr Lys Ile Lys Trp Ile
            130                 135                 140
Leu Asp Asn Val Glu Gly Ala Arg Glu Lys Ala Glu Lys Gly Glu Leu
145                 150                 155                 160
Leu Phe Gly Thr Val Asp Thr Trp Leu Val Trp Lys Leu Thr Asn Gly
                165                 170                 175
Lys Val His Val Thr Asp Tyr Thr Asn Ala Ser Arg Thr Met Leu Tyr
                180                 185                 190
Asn Ile Lys Glu Leu Lys Trp Asp Glu Arg Ile Leu Arg Lys Leu Asn
            195                 200                 205
Ile Pro Arg Ser Met Leu Pro Glu Val Lys Asn Ser Ser Glu Val Tyr
        210                 215                 220
Gly Tyr Thr Asn Leu Gly Gly Lys Gly Gly Ile Arg Val Pro Ile Ala
225                 230                 235                 240
Gly Met Ala Gly Asp Gln Gln Cys Ala Leu Phe Gly Gln Thr Cys Phe
                245                 250                 255
Glu Glu Gly Ser Val Lys Asn Thr Tyr Gly Thr Gly Cys Phe Leu Leu
            260                 265                 270
Met Asn Thr Gly Glu Asn Ile Ile Gln Ser Lys Asn Gly Leu Val Thr
        275                 280                 285
Thr Ile Ala Ile Gly Leu Glu Gly Lys Val Gln Tyr Ala Leu Glu Gly
    290                 295                 300
Ser Val Phe Val Gly Gly Ala Val Ile Gln Trp Ile Arg Asp Glu Leu
305                 310                 315                 320
Lys Leu Val Ser Asp Ala Ala Asp Thr Glu Tyr Phe Ala Lys Lys Val
                325                 330                 335
Asn Asp Asn Gly Gly Val Tyr Val Val Pro Thr Phe Thr Gly Leu Gly
            340                 345                 350
Ala Pro Tyr Trp Asp Met Tyr Ala Arg Gly Ala Ile Phe Gly Leu Thr
        355                 360                 365
Arg Gly Ala Asn Lys Asn His Ile Ile Arg Ala Ala Leu Glu Ala Ile
    370                 375                 380
Ala Tyr Gln Ser Arg Asp Leu Ile Asp Ala Met Lys Glu Asp Ser Gly
385                 390                 395                 400
Cys Glu Ile Thr Arg Ile Lys Val Asp Gly Gly Ala Ser Arg Asn Asn
                405                 410                 415
Leu Leu Met Gln Phe Gln Ala Asp Ile Thr Gly Thr Glu Val Val Arg
            420                 425                 430
Pro Ile Ile Thr Glu Thr Thr Ala Leu Gly Ala Ala Tyr Leu Ala Gly
        435                 440                 445
Leu Ala Val Gly Phe Trp Lys Ser Lys Glu Glu Ile Ala Glu Lys Trp
    450                 455                 460
Ser Val Ser Glu Val Tyr Thr Pro Asn Leu Asp Glu Asp Glu Lys Ile
465                 470                 475                 480
Arg Leu Tyr Asn Gly Trp Lys Arg Ala Val Glu Arg Val Gln Gly Trp
                485                 490                 495
Glu Glu
```

<210> SEQ ID NO 4
<211> LENGTH: 1497
<212> TYPE: DNA
<213> ORGANISM: Clostridium acetobutylicum

<400> SEQUENCE: 4

```
atgaagaaat atataatagc attagatcaa ggaactacaa gttcaagagc aataatattt      60
gaccatgaac aaaatatatt agaaattagt caaaaggaat ttactcaaat ctatccgagt     120
aaaggatggg ttgagcataa tcctttagag atatggtcaa gtcaatatgg agttttgcaa     180
gaagtaatgg caaaagctaa tataactcaa gaaaatattg cagcaatagg aattactaat     240
caaagagaaa caacaattgt ttgggacaaa aatactggag aacctgtgta taatgctatt     300
gtatggcagt gtagaagaac agcagatata gtggaaggac ttaagagaga taaagagttt     360
tcagattatg taaaagaaaa tacaggatta atattagatg catattttc agcaacaaaa     420
ataaagtgga tattagataa tgtagagggt gcaagagaaa aagctgaaaa aggtgaattg     480
ctatttggta cagttgatac ttggcttgta tggaagctaa caaatggcaa agtccatgta     540
accgattaca caaatgcatc tagaactatg ctttataata taaaggaatt aaaatgggat     600
gaaagaattt taagaaaact taatattcca agatcaatgc taccgaagt taaaaattca     660
tccgaagttt atggatatac aaaccttgga ggtaaaggtg gtattagagt accaatagca     720
ggcatggcag gagatcaaca atgtgcatta ttttggtcaaa cctgttttga agaaggtagt     780
gttaaaaata cttatggcac aggatgcttt ttacttatga atacaggaga aaatataatt     840
cagagtaaaa atggactagt aacgacaatt gcaattggat tagaagggaa agttcaatat     900
gcattagaag gttcagtgtt tgttgggggg gcagttattc agtggattag agatgaactt     960
aagttagtta gcgatgctgc ggatacagag tattttgcta aaaaagtgaa tgacaatggt    1020
ggagtatatg tggtaccaac atttactggt cttggagctc atattgggga tatgtatgct    1080
agaggagcaa ttttttggtct gacaagaggc gcaaataaaa accatataat tagagcggca    1140
cttgaagcta ttgcatatca gtcaagagat cttatagatg caatgaaaga agattcggga    1200
tgtgaaatta caagaattaa agttgatgga ggagctagta gaaataattt attaatgcag    1260
tttcaagcag acattacagg aacagaagtt gtaagaccta taataactga acaacagca    1320
cttggtgcag cttatttagc cggacttgct gtaggctttt ggaagtcaaa agaagaaatt    1380
gccgagaagt ggtctgtgag tgaggtgtat actccgaatt tagatgagga tgagaaaata    1440
agattatata cggttggaa gagagcagtt gaaagagttc agggctggga agaataa        1497
```

<210> SEQ ID NO 5
<211> LENGTH: 498
<212> TYPE: PRT
<213> ORGANISM: Clostridium acetobutylicum

<400> SEQUENCE: 5

```
Met Lys Lys Tyr Ile Ile Ala Leu Asp Gln Gly Thr Thr Ser Ser Arg
1               5                   10                  15

Ala Ile Ile Phe Asp Tyr Glu Gln Asn Ile Leu Glu Ile Ser Gln Lys
            20                  25                  30

Glu Phe Thr Gln Ile Tyr Pro Ser Lys Gly Trp Val Glu His Asn Pro
        35                  40                  45

Leu Glu Ile Trp Ser Ser Gln Tyr Gly Val Leu Gln Glu Val Met Ala
    50                  55                  60

Lys Ala Asn Ile Thr Gln Glu Asn Ile Ala Ala Ile Gly Ile Thr Asn
```

```
                65                  70                  75                  80
        Gln Arg Glu Thr Thr Ile Val Trp Asp Lys Asn Thr Gly Glu Pro Val
                            85                  90                  95

Tyr Asn Ala Ile Val Trp Gln Cys Arg Arg Thr Ala Asp Ile Val Glu
                        100                 105                 110

Gly Leu Lys Arg Asp Lys Glu Phe Ser Asp Tyr Val Lys Glu Asn Thr
                        115                 120                 125

Gly Leu Ile Leu Asp Ala Tyr Phe Ser Ala Thr Lys Ile Lys Trp Ile
                        130                 135                 140

Leu Asp Asn Val Glu Gly Ala Arg Glu Lys Ala Glu Lys Gly Glu Leu
        145                 150                 155                 160

Leu Phe Gly Thr Val Asp Thr Trp Leu Val Trp Lys Leu Thr Asn Gly
                        165                 170                 175

Lys Val His Val Thr Asp Tyr Thr Asn Ala Ser Arg Thr Met Leu Tyr
                        180                 185                 190

Asn Ile Lys Glu Leu Lys Trp Asp Glu Arg Ile Leu Arg Lys Leu Asn
                        195                 200                 205

Ile Pro Arg Ser Met Leu Pro Glu Val Lys Asn Ser Ser Glu Val Tyr
                    210                 215                 220

Gly Tyr Thr Asn Leu Gly Gly Lys Gly Gly Ile Arg Val Pro Ile Ala
        225                 230                 235                 240

Gly Met Ala Gly Asp Gln Gln Cys Ala Leu Phe Gly Gln Thr Cys Phe
                        245                 250                 255

Glu Glu Gly Ser Val Lys Asn Thr Tyr Gly Thr Gly Cys Phe Leu Leu
                    260                 265                 270

Met Asn Thr Gly Glu Asn Ile Ile Gln Ser Lys Asn Gly Leu Val Thr
                    275                 280                 285

Thr Ile Ala Ile Gly Leu Glu Gly Lys Val Gln Tyr Ala Leu Glu Gly
                    290                 295                 300

Ser Val Phe Val Gly Gly Ala Val Ile Gln Trp Ile Arg Asp Glu Leu
        305                 310                 315                 320

Lys Leu Val Ser Asp Ala Ala Asp Thr Glu Tyr Phe Ala Lys Lys Val
                        325                 330                 335

Asn Asp Asn Gly Gly Val Tyr Val Val Pro Ala Phe Thr Gly Leu Gly
                        340                 345                 350

Ala Pro Tyr Trp Asp Met Tyr Ala Arg Gly Ala Ile Phe Gly Leu Thr
                        355                 360                 365

Arg Gly Ala Asn Lys Asn His Ile Ile Arg Ala Ala Leu Glu Ala Ile
                370                 375                 380

Ala Tyr Gln Ser Arg Asp Leu Ile Asp Ala Met Lys Glu Asp Ser Gly
        385                 390                 395                 400

Cys Glu Ile Thr Arg Ile Lys Val Asp Gly Gly Ala Ser Arg Asn Asn
                        405                 410                 415

Leu Leu Met Gln Phe Gln Ala Asp Ile Thr Gly Thr Glu Val Val Arg
                        420                 425                 430

Pro Ile Ile Thr Glu Thr Thr Ala Leu Gly Ala Ala Tyr Leu Ala Gly
                    435                 440                 445

Leu Ala Val Gly Phe Trp Lys Ser Lys Glu Glu Ile Ala Glu Lys Trp
                    450                 455                 460

Ser Val Ser Glu Val Tyr Thr Pro Asn Leu Asp Glu Asp Glu Lys Ile
        465                 470                 475                 480

Arg Leu Tyr Asn Gly Trp Lys Arg Ala Val Glu Arg Val Gln Gly Trp
                        485                 490                 495
```

Glu Glu

<210> SEQ ID NO 6
<211> LENGTH: 1497
<212> TYPE: DNA
<213> ORGANISM: Clostridium acetobutylicum

<400> SEQUENCE: 6

| | | | | | |
|---|---|---|---|---|---|
| atgaagaaat | atataatagc | attagatcaa | ggaactacaa | gttcaagagc | aataatattt | 60 |
| gactatgaac | aaaatatatt | agaaattagt | caaaggaat | ttactcaaat | ctatccgagt | 120 |
| aaaggatggg | ttgagcataa | tcctttagag | atatggtcaa | gtcaatatgg | agttttgcaa | 180 |
| gaagtaatgg | caaaagctaa | tataactcaa | gaaaatattg | cagcaatagg | aattactaat | 240 |
| caaagagaaa | caacaattgt | ttgggacaaa | atactggag | aacctgtgta | taatgctatt | 300 |
| gtatggcagt | gtagaagaac | agcagatata | gtggaaggac | ttaagagaga | taaagagttt | 360 |
| tcagattatg | taaagaaaa | tacaggatta | atattagatg | catattttc | agcaacaaaa | 420 |
| ataaagtgga | tattagataa | tgtagagggt | gcaagagaaa | aagctgaaaa | aggtgaattg | 480 |
| ctatttggta | cagttgatac | ttggcttgta | tggaagctaa | caaatggcaa | agtccatgta | 540 |
| accgattaca | caaatgcatc | tagaactatg | ctttataata | taaggaatt | aaaatgggat | 600 |
| gaaagaattt | taagaaaact | taatattcca | agatcaatgc | taccagaagt | taaaaattca | 660 |
| tccgaagttt | atggatatac | aaaccttgga | ggtaaaggtg | gtattagagt | accaatagca | 720 |
| ggcatggcag | agatcaaca | atgtgcatta | tttggtcaaa | cctgttttga | agaaggtagt | 780 |
| gttaaaaata | cttatggcac | aggatgcttt | ttacttatga | atacaggaga | aaatataatt | 840 |
| cagagtaaaa | atggactagt | aacgacaatt | gcaattggat | tagaagggaa | agttcaatat | 900 |
| gcattagaag | gttcagtgtt | tgttgggggg | gcagttattc | agtggattag | agatgaactt | 960 |
| aagttagtta | gcgatgctgc | ggatacagag | tattttgcta | aaaaagtgaa | tgacaatggt | 1020 |
| ggagtatatg | tggtaccagc | atttactggt | cttggagctc | catattggga | tatgtatgct | 1080 |
| agaggagcaa | tttttggtct | gacaagaggc | gcaaataaaa | accatataat | tagagcggca | 1140 |
| cttgaagcta | ttgcatatca | gtcaagagat | cttatagatg | caatgaaaga | agattcggga | 1200 |
| tgtgaaatta | caagaattaa | agttgatgga | ggagctagta | gaaataattt | attaatgcag | 1260 |
| tttcaagcag | acattacagg | aacagaagtt | gtaagaccta | ataactgaa | acaacagca | 1320 |
| cttggtgcag | cttatttagc | cggacttgct | gtaggctttt | ggaagtcaaa | agaagaaatt | 1380 |
| gccgagaagt | ggtctgtgag | tgaggtgtat | actccgaatt | tagatgagga | tgagaaaata | 1440 |
| agattatata | acggttggaa | gagagcagtt | gaaagagttc | agggctggga | agaataa | 1497 |

<210> SEQ ID NO 7
<211> LENGTH: 498
<212> TYPE: PRT
<213> ORGANISM: Clostridium acetobutylicum

<400> SEQUENCE: 7

Met Lys Lys Tyr Ile Ile Ala Leu Asp Gln Gly Thr Thr Ser Ser Arg
1               5                   10                  15

Ala Ile Ile Phe Asp His Glu Gln Asn Ile Leu Glu Ile Ser Gln Lys
            20                  25                  30

Glu Phe Thr Gln Ile Tyr Pro Ser Lys Gly Trp Val Glu His Asn Pro
        35                  40                  45

Leu Glu Ile Trp Ser Ser Gln Tyr Gly Val Leu Gln Glu Val Met Ala

```
                50                  55                  60
Lys Ala Asn Ile Thr Gln Glu Asn Ile Ala Ala Ile Gly Ile Thr Asn
65                  70                  75                  80

Gln Arg Glu Thr Thr Ile Val Trp Asp Lys Asn Thr Gly Glu Pro Val
                85                  90                  95

Tyr Asn Ala Ile Val Trp Gln Cys Arg Thr Ala Asp Ile Val Glu
                100                 105                 110

Gly Leu Lys Arg Asp Lys Glu Phe Ser Asp Tyr Val Lys Glu Asn Thr
                115                 120                 125

Gly Leu Ile Leu Asp Ala Tyr Phe Ser Ala Thr Lys Ile Lys Trp Ile
                130                 135                 140

Leu Asp Asn Val Glu Gly Ala Arg Glu Lys Ala Glu Lys Gly Glu Leu
145                 150                 155                 160

Leu Phe Gly Thr Val Asp Thr Trp Leu Val Trp Lys Leu Thr Asn Gly
                165                 170                 175

Lys Val His Val Thr Asp Tyr Thr Asn Ala Ser Arg Thr Met Leu Tyr
                180                 185                 190

Asn Ile Lys Glu Leu Lys Trp Asp Glu Arg Ile Leu Arg Lys Leu Asn
                195                 200                 205

Ile Pro Arg Ser Met Leu Pro Glu Val Lys Asn Ser Ser Glu Val Tyr
210                 215                 220

Gly Tyr Thr Asn Leu Gly Gly Lys Gly Gly Ile Arg Val Pro Ile Ala
225                 230                 235                 240

Gly Met Ala Gly Asp Gln Gln Cys Ala Leu Phe Gly Gln Thr Cys Phe
                245                 250                 255

Glu Glu Gly Ser Val Lys Asn Thr Tyr Gly Thr Gly Cys Phe Leu Leu
                260                 265                 270

Met Asn Thr Gly Glu Asn Ile Ile Gln Ser Lys Asn Gly Leu Val Thr
                275                 280                 285

Thr Ile Ala Ile Gly Leu Glu Gly Lys Val Gln Tyr Ala Leu Glu Gly
                290                 295                 300

Ser Val Phe Val Gly Gly Ala Val Ile Gln Trp Ile Arg Asp Glu Leu
305                 310                 315                 320

Lys Leu Val Ser Asp Ala Ala Asp Thr Glu Tyr Phe Ala Lys Lys Val
                325                 330                 335

Asn Asp Asn Gly Gly Val Tyr Val Val Pro Ala Phe Thr Gly Leu Gly
                340                 345                 350

Ala Pro Tyr Trp Asp Met Tyr Ala Arg Gly Ala Ile Phe Gly Leu Thr
                355                 360                 365

Arg Gly Ala Asn Lys Asn His Ile Ile Arg Ala Ala Leu Glu Ala Ile
                370                 375                 380

Ala Tyr Gln Ser Arg Asp Leu Ile Asp Ala Met Lys Glu Asp Ser Gly
385                 390                 395                 400

Cys Glu Ile Thr Arg Ile Lys Val Asp Gly Gly Ala Ser Arg Asn Asn
                405                 410                 415

Leu Leu Met Gln Phe Gln Ala Asp Ile Thr Gly Thr Glu Val Val Arg
                420                 425                 430

Pro Ile Ile Thr Glu Thr Thr Ala Leu Gly Ala Ala Tyr Leu Ala Gly
                435                 440                 445

Leu Ala Val Gly Phe Trp Lys Ser Lys Glu Glu Ile Ala Glu Lys Trp
                450                 455                 460

Ser Met Ser Glu Val Tyr Thr Pro Asn Leu Asp Glu Asp Glu Lys Ile
465                 470                 475                 480
```

Arg Leu Tyr Asn Gly Trp Lys Arg Ala Val Glu Arg Val Gln Gly Trp
            485                 490                 495

Glu Glu

<210> SEQ ID NO 8
<211> LENGTH: 1494
<212> TYPE: DNA
<213> ORGANISM: Clostridium acetobutylicum

<400> SEQUENCE: 8

```
atgaagaaat atataatagc attagatcaa ggaactacaa gttcaagagc aataatattt    60
gaccatgaac aaaatatatt agaaattagt caaaaggaat ttactcaaat ctatccgagt   120
aaaggatggg ttgagcataa tcctttagag atatggtcaa gtcaatatgg agttttgcaa   180
gaagtaatgg caaaagctaa tataactcaa gaaaatattg cagcaatagg aattactaat   240
caaagagaaa caacaattgt ttgggacaaa aatactggag aacctgtgta taatgctatt   300
gtatggcagt gtagaagaac agcagatata gtggaaggac ttaagagaga taagagtttt   360
tcagattatg taaagaaaa tacaggatta atattagatg catattttc agcaacaaaa    420
ataaagtgga tattagataa tgtagagggt gcaagagaaa aagctgaaaa aggtgaattg   480
ctatttggta cagttgatac ttggcttgta tggaagctaa caaatggcaa agtccatgta   540
accgattaca caaatgcatc tagaactatg ctttataata taaggaatt aaaatgggat    600
gaaagaattt taagaaaact taatattcca agatcaatgc taccagaagt taaaaattca   660
tccgaagttt atggatatac aaaccttgga ggtaaaggtg gtattagagt accaatagca   720
ggcatggcag agatcaaca atgtgcatta tttggtcaaa cctgttttga agaaggtagt   780
gttaaaaata cttatggcac aggatgcttt ttacttatga atacaggaga aaatataatt   840
cagagtaaaa atggactagt aacgacaatt gcaattggat tagaagggaa agttcaatat   900
gcattagaag gttcagtgtt tgttgggggg gcagttattc agtggattag atgaaacttt   960
aagttagtta gcgatgctgc ggatacagag tattttgcta aaaaagtgaa tgacaatggt  1020
ggagtatatg tggtaccagc atttactggt cttggagctc catattggga tatgtatgct  1080
agaggagcaa tttttggtct gacaagaggc gcaaataaaa accatataat tagagcggca  1140
cttgaagcta ttgcatatca gtcaagagat cttatagatg caatgaaaga gattcggga   1200
tgtgaaatta caagaattaa agttgatgga ggagctagta gaaataattt attaatgcag  1260
tttcaagcag acattacagg aacagaagtt gtaagaccta ataactgaa caacagca     1320
cttggtgcag cttatttagc cggacttgct gtaggctttt ggaagtcaaa agaagaaatt  1380
gccgagaagt ggtctatgag tgaggtgtat actccgaatt tagatgagga tgagaaaata  1440
agattatata acggttggaa gagagcagtt gaaagagttc agggctggga agaa         1494
```

<210> SEQ ID NO 9
<211> LENGTH: 498
<212> TYPE: PRT
<213> ORGANISM: Clostridium acetobutylicum

<400> SEQUENCE: 9

Met Lys Lys Tyr Ile Ile Ala Leu Asp Gln Gly Thr Thr Ser Ser Arg
1               5                   10                  15

Ala Ile Ile Phe Asp Tyr Glu Gln Asn Ile Leu Glu Ile Ser Gln Lys
            20                  25                  30

Glu Phe Thr Gln Ile Tyr Pro Ser Lys Gly Trp Val Glu His Asn Pro

```
                35                  40                  45
Leu Glu Ile Trp Ser Ser Gln Tyr Gly Val Leu Gln Glu Val Met Ala
 50                  55                  60

Lys Ala Asn Ile Thr Gln Glu Asn Ile Ala Ala Ile Gly Ile Thr Asn
 65                  70                  75                  80

Gln Arg Glu Thr Thr Ile Val Trp Asp Lys Asn Thr Gly Glu Pro Val
                 85                  90                  95

Tyr Asn Ala Ile Val Trp Gln Cys Arg Arg Thr Ala Asp Ile Val Glu
                100                 105                 110

Gly Leu Lys Arg Asp Lys Glu Phe Ser Asp Tyr Val Lys Glu Asn Thr
                115                 120                 125

Gly Leu Ile Leu Asp Ala Tyr Phe Ser Ala Thr Lys Ile Lys Trp Ile
            130                 135                 140

Leu Asp Asn Val Glu Gly Ala Arg Glu Lys Ala Glu Lys Gly Glu Leu
145                 150                 155                 160

Leu Phe Gly Thr Val Asp Thr Trp Leu Val Trp Lys Leu Thr Asn Gly
                165                 170                 175

Lys Val His Val Thr Asp Tyr Thr Asn Ala Ser Arg Thr Met Leu Tyr
                180                 185                 190

Asn Ile Lys Glu Leu Lys Trp Asp Glu Arg Ile Leu Arg Lys Leu Asn
            195                 200                 205

Ile Pro Arg Ser Met Leu Pro Glu Val Lys Asn Ser Ser Glu Val Tyr
210                 215                 220

Gly Tyr Thr Asn Leu Gly Gly Lys Gly Gly Ile Arg Val Pro Ile Ala
225                 230                 235                 240

Gly Met Ala Gly Asp Gln Gln Cys Ala Leu Phe Gly Gln Thr Cys Phe
                245                 250                 255

Glu Glu Gly Ser Val Lys Asn Thr Tyr Gly Thr Gly Cys Phe Leu Leu
                260                 265                 270

Met Asn Thr Gly Glu Asn Ile Ile Gln Ser Lys Asn Gly Leu Val Thr
            275                 280                 285

Thr Ile Ala Ile Gly Leu Glu Gly Lys Val Gln Tyr Ala Leu Glu Gly
290                 295                 300

Ser Val Phe Val Gly Gly Ala Val Ile Gln Trp Ile Arg Asp Glu Leu
305                 310                 315                 320

Lys Leu Val Ser Asp Ala Asp Thr Glu Tyr Phe Ala Lys Lys Val
                325                 330                 335

Asn Asp Asn Gly Gly Val Tyr Val Val Pro Thr Phe Thr Gly Leu Gly
                340                 345                 350

Ala Pro Tyr Trp Asp Met Tyr Ala Arg Gly Ala Ile Phe Gly Leu Thr
            355                 360                 365

Arg Gly Ala Asn Lys Asn His Ile Ile Arg Ala Ala Leu Glu Ala Ile
            370                 375                 380

Ala Tyr Gln Ser Arg Asp Leu Ile Asp Ala Met Lys Glu Asp Ser Gly
385                 390                 395                 400

Cys Glu Ile Thr Arg Ile Lys Val Asp Gly Gly Ala Ser Arg Asn Asn
                405                 410                 415

Leu Leu Met Gln Phe Gln Ala Asp Ile Thr Gly Thr Glu Val Val Arg
                420                 425                 430

Pro Ile Ile Thr Glu Thr Thr Ala Leu Gly Ala Ala Tyr Leu Ala Gly
            435                 440                 445

Leu Ala Val Gly Phe Trp Lys Ser Lys Glu Glu Ile Ala Glu Lys Trp
450                 455                 460
```

```
Ser Val Ser Glu Val Tyr Thr Pro Asn Leu Asp Glu Asp Glu Lys Ile
465                 470                 475                 480

Arg Leu Tyr Asn Gly Trp Lys Arg Ala Val Glu Arg Val Gln Gly Trp
            485                 490                 495

Glu Glu

<210> SEQ ID NO 10
<211> LENGTH: 1497
<212> TYPE: DNA
<213> ORGANISM: Clostridium acetobutylicum

<400> SEQUENCE: 10
atgaagaaat atataatagc attagatcaa ggaactacaa gttcaagagc aataatattt      60
gactatgaac aaaatatatt agaaattagt caaaaggaat ttactcaaat ctatccgagt     120
aaaggatggg ttgagcataa tcctttagag atatggtcaa gtcaatatgg agttttgcaa     180
gaagtaatgg caaagctaa tataactcaa gaaaatattg cagcaatagg aattactaat     240
caaagagaaa caacaattgt ttgggacaaa atactggag aacctgtgta atgctatt       300 gtatggcagt gtagaagaac agcagatata gtggaaggac ttaagagaga taaagagttt     360
tcagattatg taaaagaaaa tacaggatta atattagatg catattttc agcaacaaaa     420 ataaagtgga tattagataa tgtagagggt gcaagagaaa aagctgaaaa aggtgaattg     480
ctatttggta cagttgatac ttggcttgta tggaagctaa caaatggcaa agtccatgta     540
accgattaca caaatgcatc tagaactatg ctttataata taaggaatt aaaatgggat     600 gaaagaattt taagaaaact taatattcca agatcaatgc taccagaagt taaaaattca     660
tccgaagttt atgatatac aaaccttgga ggtaaaggtg gtattagagt accaatagca     720
ggcatggcag gagatcaaca atgtgcatta tttggtcaaa cctgttttga agaaggtagt     780
gttaaaaata cttatggcac aggatgcttt ttacttatga atacaggaga aaatataatt     840
cagagtaaaa atggactagt aacgacaatt gcaattggat tagaagggaa agttcaatat     900
gcattagaag gttcagtgtt tgttgggggg gcagttattc agtggattag atgtgaactt     960
aagttagtta gcgatgctgc ggatacagag tattttgcta aaaaagtgaa tgacaatggt    1020
ggagtatatg tggtaccaac atttactggt cttggagctc atattgggga tatgtatgct    1080
agaggagcaa tttttggtct gacaagaggc gcaaataaaa accatataat tagagcggca    1140
cttgaagcta ttgcatatca gtcaagagat cttatagatg caatgaaaga agattcggga    1200
tgtgaaatta caagaattaa agttgatgga ggagctagta gaaataattt attaatgcag    1260
tttcaagcag acattacagg aacagaagtt gtaagaccta taataactga acaacagca     1320 cttggtgcag cttatttagc cggacttgct gtaggctttt ggaagtcaaa agaagaaatt    1380
gccgagaagt ggtctgtgag tgaggtgtat actccgaatt tagatgagga tgagaaaata    1440
agattatata acggttggaa gagagcagtt gaaagagttc agggctggga agaataa       1497

<210> SEQ ID NO 11
<211> LENGTH: 498
<212> TYPE: PRT
<213> ORGANISM: Clostridium acetobutylicum

<400> SEQUENCE: 11

Met Lys Lys Tyr Ile Ile Ala Leu Asp Gln Gly Thr Thr Ser Ser Arg
1               5                  10                  15

Ala Ile Ile Phe Asp His Glu Gln Asn Ile Leu Glu Ile Ser Gln Lys
```

```
                20                  25                  30
Glu Phe Thr Gln Ile Tyr Pro Ser Lys Gly Trp Val Glu His Asn Pro
            35                  40                  45
Leu Glu Ile Trp Ser Ser Gln Tyr Gly Val Leu Gln Glu Val Met Ala
        50                  55                  60
Lys Ala Asn Ile Thr Gln Glu Asn Ile Ala Ala Ile Gly Ile Thr Asn
65                  70                  75                  80
Gln Arg Glu Thr Thr Ile Val Trp Asp Lys Asn Thr Gly Glu Pro Val
                85                  90                  95
Tyr Asn Ala Ile Val Trp Gln Cys Arg Arg Thr Ala Asp Ile Val Glu
            100                 105                 110
Gly Leu Lys Arg Asp Lys Glu Phe Ser Asp Tyr Val Lys Glu Asn Thr
            115                 120                 125
Gly Leu Ile Leu Asp Ala Tyr Phe Ser Ala Thr Lys Ile Lys Trp Ile
        130                 135                 140
Leu Asp Asn Val Glu Gly Ala Arg Glu Lys Ala Glu Lys Gly Glu Leu
145                 150                 155                 160
Leu Phe Gly Thr Val Asp Thr Trp Leu Val Trp Lys Leu Thr Asn Gly
                165                 170                 175
Lys Val His Val Thr Asp Tyr Thr Asn Ala Ser Arg Thr Met Leu Tyr
            180                 185                 190
Asn Ile Lys Glu Leu Lys Trp Asp Glu Arg Ile Leu Arg Lys Leu Asn
            195                 200                 205
Ile Pro Arg Ser Met Leu Pro Glu Val Lys Asn Ser Ser Glu Val Tyr
        210                 215                 220
Gly Tyr Thr Asn Leu Gly Gly Lys Gly Gly Ile Arg Val Pro Ile Ala
225                 230                 235                 240
Gly Met Ala Gly Asp Gln Gln Cys Ala Leu Phe Gly Gln Thr Cys Phe
                245                 250                 255
Glu Glu Gly Ser Val Lys Asn Thr Tyr Gly Thr Gly Cys Phe Leu Leu
            260                 265                 270
Met Asn Thr Gly Glu Asn Ile Ile Gln Ser Lys Asn Gly Leu Val Thr
            275                 280                 285
Thr Ile Ala Ile Gly Leu Glu Gly Lys Val Gln Tyr Ala Leu Glu Gly
        290                 295                 300
Ser Val Phe Val Gly Gly Ala Val Ile Gln Trp Ile Arg Asp Glu Leu
305                 310                 315                 320
Lys Leu Val Ser Asp Ala Ala Asp Thr Glu Tyr Phe Ala Lys Lys Val
                325                 330                 335
Asn Asp Asn Gly Gly Val Tyr Val Val Pro Thr Phe Thr Gly Leu Gly
            340                 345                 350
Ala Pro Tyr Trp Asp Met Tyr Ala Arg Gly Ala Ile Phe Gly Leu Thr
            355                 360                 365
Arg Gly Ala Asn Lys Asn His Ile Ile Arg Ala Ala Leu Glu Ala Ile
        370                 375                 380
Ala Tyr Gln Ser Arg Asp Leu Ile Asp Ala Met Lys Glu Asp Ser Gly
385                 390                 395                 400
Cys Glu Ile Thr Arg Ile Lys Val Asp Gly Gly Ala Ser Arg Asn Asn
                405                 410                 415
Leu Leu Met Gln Phe Gln Ala Asp Ile Thr Gly Thr Glu Val Val Arg
            420                 425                 430
Pro Ile Ile Thr Glu Thr Thr Ala Leu Gly Ala Ala Tyr Leu Ala Gly
        435                 440                 445
```

```
Leu Ala Val Gly Phe Trp Lys Ser Lys Glu Glu Ile Ala Glu Lys Trp
    450                 455                 460

Ser Met Ser Glu Val Tyr Thr Pro Asn Leu Asp Glu Asp Glu Lys Ile
465                 470                 475                 480

Arg Leu Tyr Asn Gly Trp Lys Arg Ala Val Arg Val Gln Gly Trp
                485                 490                 495

Glu Glu

<210> SEQ ID NO 12
<211> LENGTH: 1497
<212> TYPE: DNA
<213> ORGANISM: Clostridium acetobutylicum

<400> SEQUENCE: 12
atgaagaaat atataatagc attagatcaa ggaactacaa gttcaagagc aataatattt      60
gaccatgaac aaaatatatt agaaattagt caaaaggaat ttactcaaat ctatccgagt     120
aaaggatggg ttgagcataa tcctttagag atatggtcaa gtcaatatgg agttttgcaa     180
gaagtaatgg caaaagctaa tataactcaa gaaatattg cagcaatagg aattactaat      240
caaagagaaa caacaattgt ttgggacaaa atactggaa aacctgtgta taatgctatt      300
gtatggcagt gtagaagaac agcagatata gtggaaggac ttaagagaga taaagagttt     360
tcagattatg taaaagaaaa tacaggatta atattgatg catattttc agcaacaaaa       420 ataaagtgga tattagataa tgtagagggt gcaagagaaa aagctgaaaa aggtgaattg     480
ctatttggta cagttgatac ttggcttgta tggaagctaa caaatggcaa agtccatgta     540
accgattaca caaatgcatc tagaactatg ctttataata taaggaatt aaaatgggat      600 gaaagaattt taagaaaact taatattcca agatcaatgc taccgaagt taaaaattca      660 tccgaagttt atggatatac aaaccttgga ggtaaaggtg gtattagagt accaatagca     720
ggcatggcag agatcaaca atgtgcatta tttggtcaaa cctgttttga agaaggtagt      780
gttaaaaata cttatggcac aggatgcttt ttacttatga atacaggaga aaatataatt     840
cagagtaaaa atggactagt aacgacaatt gcaattggat tagaagggaa agttcaatat     900
gcattagaag gttcagtgtt tgttgggggg gcagttattc agtggattag atgtgaactt     960
aagttagtta gcgatgctgc ggatacagag tattttgcta aaaaagtgaa tgacaatggt    1020
ggagtatatg tggtaccaac atttactggt cttggagctc atattgggga tatgtatgct    1080
agaggagcaa tttttggtct gacaagaggc gcaaatataaaa accatataat tagagcggca    1140
cttgaagcta ttgcatatca gtcaagagat cttatagatg caatgaaaga agattcggga    1200
tgtgaaatta caagaattaa agttgatgga ggagctagta aaataatttt attaatgcag    1260
tttcaagcag acattacagg aacagaagtt gtaagaccta taactgaa caacagca        1320 cttggtgcag cttatttagc cggacttgct gtaggcttt ggaagtcaaa agaagaaatt    1380
gccgagaagt ggtctatgag tgaggtgtat actccgaatt tagatgagga tgagaaaata    1440
agattatata acggttggaa gagagcagtt gaaagagttc agggctggga agaataa       1497

<210> SEQ ID NO 13
<211> LENGTH: 498
<212> TYPE: PRT
<213> ORGANISM: Clostridium acetobutylicum

<400> SEQUENCE: 13

Met Lys Lys Tyr Ile Ile Ala Leu Asp Gln Gly Thr Thr Ser Ser Arg
```

```
  1               5                    10                   15
Ala Ile Ile Phe Asp Tyr Glu Gln Asn Ile Leu Glu Ile Ser Gln Lys
            20                   25                  30
Glu Phe Thr Gln Ile Tyr Pro Ser Lys Gly Trp Val Glu His Asn Pro
            35                   40                  45
Leu Glu Ile Trp Ser Ser Gln Tyr Gly Val Leu Gln Glu Val Met Ala
 50                   55                  60
Lys Ala Asn Ile Thr Gln Glu Asn Ile Ala Ala Ile Gly Ile Thr Asn
 65                   70                  75                  80
Gln Arg Glu Thr Thr Ile Val Trp Asp Lys Asn Thr Gly Glu Pro Val
            85                   90                  95
Tyr Asn Ala Ile Val Trp Gln Cys Arg Arg Thr Ala Asp Ile Val Glu
            100                  105                 110
Gly Leu Lys Arg Asp Lys Glu Phe Ser Asp Tyr Val Lys Glu Asn Thr
            115                  120                 125
Gly Leu Ile Leu Asp Ala Tyr Phe Ser Ala Thr Lys Ile Lys Trp Ile
            130                  135                 140
Leu Asp Asn Val Glu Gly Ala Arg Glu Lys Ala Glu Lys Gly Glu Leu
145                  150                  155                 160
Leu Phe Gly Thr Val Asp Thr Trp Leu Val Trp Lys Leu Thr Asn Gly
            165                  170                 175
Lys Val His Val Thr Asp Tyr Thr Asn Ala Ser Arg Thr Met Leu Tyr
            180                  185                 190
Asn Ile Lys Glu Leu Lys Trp Asp Glu Arg Ile Leu Arg Lys Leu Asn
            195                  200                 205
Ile Pro Arg Ser Met Leu Pro Glu Val Lys Asn Ser Ser Glu Val Tyr
210                  215                  220
Gly Tyr Thr Asn Leu Gly Gly Lys Gly Ile Arg Val Pro Ile Ala
225                  230                  235                 240
Gly Met Ala Gly Asp Gln Gln Cys Ala Leu Phe Gly Gln Thr Cys Phe
            245                  250                 255
Glu Glu Gly Ser Val Lys Asn Thr Tyr Gly Thr Gly Cys Phe Leu Leu
            260                  265                 270
Met Asn Thr Gly Glu Asn Ile Ile Gln Ser Lys Asn Gly Leu Val Thr
            275                  280                 285
Thr Ile Ala Ile Gly Leu Glu Gly Lys Val Gln Tyr Ala Leu Glu Gly
            290                  295                 300
Ser Val Phe Val Gly Gly Ala Val Ile Gln Trp Ile Arg Asp Glu Leu
305                  310                  315                 320
Lys Leu Val Ser Asp Ala Ala Asp Thr Glu Tyr Phe Ala Lys Lys Val
            325                  330                 335
Asn Asp Asn Gly Gly Val Tyr Val Pro Thr Phe Thr Gly Leu Gly
            340                  345                 350
Ala Pro Tyr Trp Asp Met Tyr Ala Arg Gly Ala Ile Phe Gly Leu Thr
            355                  360                 365
Arg Gly Ala Asn Lys Asn His Ile Ile Arg Ala Ala Leu Glu Ala Ile
            370                  375                 380
Ala Tyr Gln Ser Arg Asp Leu Ile Asp Ala Met Lys Glu Asp Ser Gly
385                  390                  395                 400
Cys Glu Ile Thr Arg Ile Lys Val Asp Gly Gly Ala Ser Arg Asn Asn
            405                  410                 415
Leu Leu Met Gln Phe Gln Ala Asp Ile Thr Gly Thr Glu Val Val Arg
            420                  425                 430
```

```
Pro Ile Ile Thr Glu Thr Thr Ala Leu Gly Ala Ala Tyr Leu Ala Gly
        435                 440                 445

Leu Ala Val Gly Phe Trp Lys Ser Lys Glu Glu Ile Ala Glu Lys Trp
    450                 455                 460

Ser Met Ser Glu Val Tyr Thr Pro Asn Leu Asp Glu Asp Glu Lys Ile
465                 470                 475                 480

Arg Leu Tyr Asn Gly Trp Lys Arg Ala Val Glu Arg Val Gln Gly Trp
                485                 490                 495

Glu Glu

<210> SEQ ID NO 14
<211> LENGTH: 1497
<212> TYPE: DNA
<213> ORGANISM: Clostridium acetobutylicum

<400> SEQUENCE: 14
atgaagaaat atataatagc attagatcaa ggaactacaa gttcaagagc aataatattt      60
gactatgaac aaaatatatt agaaattagt caaaaggaat ttactcaaat ctatccgagt     120
aaaggatggg ttgagcataa tcctttagag atatggtcaa gtcaatatgg agttttgcaa     180
gaagtaatgg caaaagctaa tataactcaa gaaaatattg cagcaatagg aattactaat     240
caaagagaaa caacaattgt ttgggacaaa aatactggag aacctgtgta taatgctatt     300
gtatggcagt gtagaagaac agcagatata gtggaaggac ttaagagaga taaagagttt     360
tcagattatg taaagaaaa tacaggatta atattagatg catattttc agcaacaaaa      420 ataaagtgga tattagataa tgtagagggt gcaagagaaa aagctgaaaa aggtgaattg     480
ctatttggta cagttgatac ttggcttgta tggaagctaa caaatggcaa agtccatgta     540
accgattaca caaatgcatc tagaactatg ctttataata taaggaatt aaaatgggat     600 gaaagaattt taagaaaact taatattcca agatcaatgc taccagaagt taaaaattca     660
tccgaagttt atggatatac aaaccttgga ggtaaaggtg gtattagagt accaatagca     720
ggcatggcag gagatcaaca atgtgcatta tttggtcaaa cctgttttga agaaggtagt     780
gttaaaaata cttatggcac aggatgctt ttacttatga atacaggaga aaatataatt      840
cagagtaaaa atggactagt aacgacaatt gcaattggat tagaagggaa agttcaatat     900
gcattagaag gttcagtgtt tgttgggggg gcagttattc agtggattag atgaacttt      960 aagttagtta gcgatgctgc ggatacagag tattttgcta aaaaagtgaa tgacaatggt    1020
ggagtatatg tggtaccaac atttactggt cttggagctc atattgggga tatgtatgct    1080
agaggagcaa tttttggtct gacaagaggc gcaaataaaa accatataat tagagcggca    1140
cttgaagcta ttgcatatca gtcaagagat cttatagatg caatgaaaga agattcggga    1200
tgtgaaatta caagaattaa agttgatgga ggagctagta gaaataattt attaatgcag    1260
tttcaagcag acattacagg aacagaagtt gtaagaccta ataactgaa caacagca      1320 cttggtgcag cttatttagc cggacttgct gtaggctttt ggaagtcaaa agaagaaatt    1380
gccgagaagt ggtctatgag tgaggtgtat actccgaatt tagatgagga tgagaaaata    1440
agattatata cggttggaa gagagcagtt gaaagagttc agggctggga agaataa         1497

<210> SEQ ID NO 15
<211> LENGTH: 582
<212> TYPE: PRT
<213> ORGANISM: Clostridium acetobutylicum
```

```
<400> SEQUENCE: 15

Met Lys Thr Ile Ile Leu Asn Gly Asn Glu Val His Thr Asp Lys Asp
1               5                   10                  15

Ile Thr Ile Leu Glu Leu Ala Arg Glu Asn Asn Val Asp Ile Pro Thr
            20                  25                  30

Leu Cys Phe Leu Lys Asp Cys Gly Asn Phe Gly Lys Cys Gly Val Cys
        35                  40                  45

Met Val Glu Val Glu Gly Lys Gly Phe Arg Ala Ala Cys Val Ala Lys
    50                  55                  60

Val Glu Asp Gly Met Val Ile Asn Thr Glu Ser Asp Glu Val Lys Glu
65                  70                  75                  80

Arg Ile Lys Lys Arg Val Ser Met Leu Leu Asp Lys His Glu Phe Lys
                85                  90                  95

Cys Gly Gln Cys Ser Arg Arg Glu Asn Cys Glu Phe Leu Lys Leu Val
            100                 105                 110

Ile Lys Thr Lys Ala Lys Ala Ser Lys Pro Phe Leu Pro Glu Asp Lys
        115                 120                 125

Asp Ala Leu Val Asp Asn Arg Ser Lys Ala Ile Val Ile Asp Arg Ser
130                 135                 140

Lys Cys Val Leu Cys Gly Arg Cys Val Ala Ala Cys Lys Gln His Thr
145                 150                 155                 160

Ser Thr Cys Ser Ile Gln Phe Ile Lys Lys Asp Gly Gln Arg Ala Val
                165                 170                 175

Gly Thr Val Asp Asp Val Cys Leu Asp Asp Ser Thr Cys Leu Leu Cys
            180                 185                 190

Gly Gln Cys Val Ile Ala Cys Pro Val Ala Ala Leu Lys Glu Lys Ser
        195                 200                 205

His Ile Glu Lys Val Gln Glu Ala Leu Asn Asp Pro Lys Lys His Val
    210                 215                 220

Ile Val Ala Met Ala Pro Ser Val Arg Thr Ala Met Gly Glu Leu Phe
225                 230                 235                 240

Lys Met Gly Tyr Gly Lys Asp Val Thr Gly Lys Leu Tyr Thr Ala Leu
                245                 250                 255

Arg Met Leu Gly Phe Asp Lys Val Phe Asp Ile Asn Phe Gly Ala Asp
            260                 265                 270

Met Thr Ile Met Glu Glu Ala Thr Glu Leu Leu Gly Arg Val Lys Asn
        275                 280                 285

Asn Gly Pro Phe Pro Met Phe Thr Ser Cys Cys Pro Ala Trp Val Arg
290                 295                 300

Leu Ala Gln Asn Tyr His Pro Glu Leu Leu Asp Asn Leu Ser Ser Ala
305                 310                 315                 320

Lys Ser Pro Gln Gln Ile Phe Gly Thr Ala Ser Lys Thr Tyr Tyr Pro
                325                 330                 335

Ser Ile Ser Gly Ile Ala Pro Glu Asp Val Tyr Thr Val Thr Ile Met
            340                 345                 350

Pro Cys Asn Asp Lys Lys Tyr Glu Ala Asp Ile Pro Phe Met Glu Thr
        355                 360                 365

Asn Ser Leu Arg Asp Ile Asp Ala Ser Leu Thr Thr Arg Glu Leu Ala
370                 375                 380

Lys Met Ile Lys Asp Ala Lys Ile Lys Phe Ala Asp Leu Glu Asp Gly
385                 390                 395                 400

Glu Val Asp Pro Ala Met Gly Thr Tyr Ser Gly Ala Gly Ala Ile Phe
                405                 410                 415
```

```
Gly Ala Thr Gly Gly Val Met Glu Ala Ala Ile Arg Ser Ala Lys Asp
            420                 425                 430
Phe Ala Glu Asn Lys Glu Leu Glu Asn Val Asp Tyr Thr Glu Val Arg
            435                 440                 445
Gly Phe Lys Gly Ile Lys Glu Ala Glu Val Glu Ile Ala Gly Asn Lys
            450                 455                 460
Leu Asn Val Ala Val Ile Asn Gly Ala Ser Asn Phe Glu Phe Met
465                 470                 475                 480
Lys Ser Gly Lys Met Asn Glu Lys Gln Tyr His Phe Ile Glu Val Met
            485                 490                 495
Ala Cys Pro Gly Gly Cys Ile Asn Gly Gly Gln Pro His Val Asn
            500                 505                 510
Ala Leu Asp Arg Glu Asn Val Asp Tyr Arg Lys Leu Arg Ala Ser Val
            515                 520                 525
Leu Tyr Asn Gln Asp Lys Asn Val Leu Ser Lys Arg Lys Ser His Asp
            530                 535                 540
Asn Pro Ala Ile Ile Lys Met Tyr Asp Ser Tyr Phe Gly Lys Pro Gly
545                 550                 555                 560
Glu Gly Leu Ala His Lys Leu Leu His Val Lys Tyr Thr Lys Asp Lys
            565                 570                 575
Asn Val Ser Lys His Glu
            580

<210> SEQ ID NO 16
<211> LENGTH: 1749
<212> TYPE: DNA
<213> ORGANISM: Clostridium acetobutylicum

<400> SEQUENCE: 16
atgaaaacaa taatcttaaa tggcaatgaa gtgcatacag ataaagatat tactatcctt     60
gagctagcaa gagaaaataa tgtagatatc ccaacactct gcttttaaa ggattgtggc    120 aattttggaa atgcggagt ctgtatggta gaggtagaag gcaagggctt tagagctgct    180
tgtgttgcca agttgaaga tggaatggta ataaacacag aatccgatga agtaaaagaa    240
cgaatcaaaa aaagagtttc aatgcttctt gataagcatg aatttaaatg tggacaatgt    300
tctagaagag aaaattgtga attccttaaa cttgtaataa agacaaaagc aaaagcttca    360
aaaccatttt taccagaaga taaggatgct ctagttgata atagaagtaa ggctattgta    420
attgacagat caaaatgtgt actatgcggt agatgcgtag ctgcatgtaa acagcacaca    480
agcacttgct caattcaatt tattaaaaaa gatggacaaa gggctgttgg aactgttgat    540
gatgtttgtc ttgatgactc aacatgctta ttatgcggtc agtgtgtaat cgcttgtcct    600
gttgctgctt aaaagaaaa atcccatata gaaaagttc aagaagctct taatgaccct    660
aaaaaacatg tcattgttgc aatggctcca tcagtaagaa ctgctatggg cgaattattc    720
aaaatgggat atgaaaaga gtaacagga aaactatata ctgcacttag aatgttaggc    780
tttgataaag tatttgatat aaactttggt gcagatatga ctataatgga agaagctact    840
gaacttttag gcagagttaa aaataatggc ccattcccta tgtttacatc ttgctgtcct    900
gcatgggtaa gattagctca aaattatcat cctgaattat tagataatct ttcatcagca    960
aaatcaccac aacaaatatt tggtactgca tcaaaaactt actatccttc aatttcagga   1020
atagctccag aagatgttta tacagttact atcatgcctt gtaatgataa aaatatgaa   1080 gcagatattc ctttcatgga aactaacagc ttaagagata ttgatgcatc cttaactaca   1140
```

```
agagagcttg caaaaatgat taaagatgca aaaattaaat ttgcagatct tgaagatggt   1200
gaagttgatc ctgctatggg tacttacagt ggtgctggag ctatctttgg tgcaaccggt   1260
ggcgttatgg aagctgcaat aagatcagct aaagactttg ctgaaaataa agaacttgaa   1320
aatgttgatt acactgaagt aagaggcttt aaaggcataa agaagcgga agttgaaatt   1380 gctggaaata actaaacgt tgctgttata atggtgctt ctaacttctt cgagtttatg   1440
aaatctggaa aaatgaacga aaacaatat cactttatag aagtaatggc ttgccctggt   1500
ggatgtataa atggtggagg tcaacctcac gtaaatgctc ttgatagaga aatgttgat   1560 tacagaaaac taagagcatc agtattatac aaccaagata aaaatgttct ttcaaagaga   1620
aagtcacatg ataatccagc tattattaaa atgtatgata gctactttgg aaaaccaggt   1680
gaaggacttg ctcacaaatt actacacgta aaatacacaa aagataaaaa tgtttcaaaa   1740
catgaataa                                                           1749
```

<210> SEQ ID NO 17
<211> LENGTH: 209
<212> TYPE: PRT
<213> ORGANISM: Clostridium acetobutylicum

<400> SEQUENCE: 17

```
Met Lys Thr Ile Ile Leu Asn Gly Asn Glu Val His Thr Asp Lys Asp
1               5                   10                  15

Ile Thr Ile Leu Glu Leu Ala Arg Glu Asn Asn Val Asp Ile Pro Thr
            20                  25                  30

Leu Cys Phe Leu Lys Asp Cys Gly Asn Phe Gly Lys Cys Gly Val Cys
        35                  40                  45

Met Val Glu Val Glu Gly Lys Gly Phe Arg Ala Ala Cys Val Ala Lys
    50                  55                  60

Val Glu Asp Gly Met Val Ile Asn Thr Glu Ser Asp Glu Val Lys Glu
65                  70                  75                  80

Arg Ile Lys Lys Arg Val Ser Met Leu Leu Asp Lys His Glu Phe Lys
                85                  90                  95

Cys Gly Gln Cys Ser Arg Arg Glu Asn Cys Glu Phe Leu Lys Leu Val
            100                 105                 110

Ile Lys Thr Lys Ala Lys Ala Ser Lys Pro Phe Leu Pro Glu Asp Lys
        115                 120                 125

Asp Ala Leu Val Asp Asn Arg Ser Lys Ala Ile Val Ile Asp Arg Ser
    130                 135                 140

Lys Cys Val Leu Cys Gly Arg Cys Val Ala Ala Cys Lys Gln His Thr
145                 150                 155                 160

Ser Thr Cys Ser Ile Gln Phe Ile Lys Lys Asp Gly Gln Arg Ala Val
                165                 170                 175

Gly Thr Val Asp Asp Val Cys Leu Asp Asp Ser Thr Cys Leu Leu Cys
            180                 185                 190

Gly Gln Cys Val Ile Ala Cys Pro Val Ala Ala Leu Lys Lys Asn Pro
        195                 200                 205

Ile
```

<210> SEQ ID NO 18
<211> LENGTH: 630
<212> TYPE: DNA
<213> ORGANISM: Clostridium acetobutylicum

<400> SEQUENCE: 18

```
atgaaaacaa taatcttaaa tggcaatgaa gtgcatacag ataaagatat tactatcctt     60
gagctagcaa gagaaaataa tgtagatatc ccaacactct gcttttaaa ggattgtggc    120 aattttggaa atgcggagt ctgtatggta gaggtagaag gcaagggctt tagagctgct    180
tgtgttgcca agttgaaga tggaatggta ataaacacag aatccgatga agtaaaagaa    240
cgaatcaaaa aaagagtttc aatgcttctt gataagcatg aatttaaatg tggacaatgt    300
tctagaagag aaaattgtga attccttaaa cttgtaataa agacaaaagc aaagcttca    360 aaaccatttt taccagaaga taaggatgct ctagttgata atagaagtaa ggctattgta    420
attgacagat caaatgtgt actatgcggt agatgcgtag ctgcatgtaa acagcacaca    480
agcacttgct caattcaatt tattaaaaaa gatggacaaa gggctgttgg aactgttgat    540
gatgtttgtc ttgatgactc aacatgctta ttatgcggtc agtgtgtaat cgcttgtcct    600
gttgctgctt taaaaaaaaa tcccatatag                                    630
```

<210> SEQ ID NO 19
<211> LENGTH: 242
<212> TYPE: PRT
<213> ORGANISM: Clostridium acetobutylicum

<400> SEQUENCE: 19

```
Met His Tyr Ser Leu Ala Val Lys Leu Val Cys Glu Met Leu Gly Thr
1               5                   10                  15

Ala Ile Leu Val Leu Phe Gly Asn Gly Ala Val Ala Asn Val Glu Leu
                20                  25                  30

Lys Gly Thr Lys Gly Tyr Arg Asn Gly Trp Ile Ile Ala Ile Gly
        35                  40                  45

Tyr Gly Val Gly Val Met Leu Pro Ala Leu Met Phe Asn Lys Ile Ser
    50                  55                  60

Gly Ser Gln Thr Asn Pro Ala Met Thr Ile Gly Leu Ala Val Asn Gly
65                  70                  75                  80

Leu Phe Pro Trp Ser Glu Val Ile Pro Tyr Ile Leu Ala Gln Phe Val
                85                  90                  95

Gly Ala Ile Ile Gly Gln Val Ile Leu Tyr Phe Ile Tyr Leu Pro Phe
            100                 105                 110

Tyr Lys Gln Thr Glu Asp Thr Lys Ser Ile Leu Gly Thr Cys Ser Thr
        115                 120                 125

Ile Ser Ala Ser Gly Ser His Ile Asn Gly Phe Val Thr Glu Phe Phe
    130                 135                 140

Gly Thr Phe Leu Leu Val Leu Gly Ala Met Phe Ile Leu Asn Ser Thr
145                 150                 155                 160

Gly Val Lys Ser Thr Pro Ala Val Gly Tyr Val Gly Leu Gly Phe Leu
                165                 170                 175

Val Cys Ser Leu Val Ala Ser Leu Gly Gly Pro Thr Gly Pro Gly Leu
            180                 185                 190

Asn Pro Ala Arg Asp Leu Gly Pro Arg Ile Val His Ser Leu Leu Pro
        195                 200                 205

Leu Lys Asn Lys Gly Asn Ser Glu Trp Thr Tyr Ala Trp Ile Pro Val
    210                 215                 220

Leu Ala Pro Met Phe Gly Ser Ile Ile Ala Ile Phe Leu Phe Asn Lys
225                 230                 235                 240

Ile Tyr
```

-continued

```
<210> SEQ ID NO 20
<211> LENGTH: 729
<212> TYPE: DNA
<213> ORGANISM: Clostridium acetobutylicum

<400> SEQUENCE: 20
atgcattata gtttagctgt aaagttagtt tgcgaaatgc ttggtacagc aattttagta      60
ctatttggta acggtgcagt tgctaatgta gaattaaaag gaactaaagg gtatcgcaat     120
ggctggatta ttattgccat tggttatggt gttggtgtaa tgcttccagc tttaatgttt     180
aataaaatta gtggtagtca gacaaatcca gctatgacaa taggattagc agtaaatggg     240 cttttttccgt ggtctgaggt tataccatat atattggctc agtttgtagg tgctataata     300
ggtcaagtta ttctttactt tatatacctt ccgttttata acaaacaga ggatactaaa      360 agcattcttg gtacatgttc tactatatca gcatcaggaa gtcatataaa tggatttgtc     420
acagaatttt ttggcacatt cttattggtt ttaggtgcaa tgtttattct taattcaact     480
ggagtaaaaa gtacacctgc agtaggttat gttggtcttg gatttcttgt atgctcatta     540
gttgcatctt aggtggtcc aactggtcct ggattaaatc cagctagaga tttgggccct     600
cgtatagtac attcactttt gccacttaaa aataaaggca attctgaatg gacatatgcc     660
tggattcctg ttttggcacc aatgtttgga agtattattg ctatattctt gtttaataaa     720
atatattaa                                                             729

<210> SEQ ID NO 21
<211> LENGTH: 242
<212> TYPE: PRT
<213> ORGANISM: Clostridium acetobutylicum

<400> SEQUENCE: 21

Met His Tyr Ser Leu Ala Val Lys Leu Val Cys Glu Ile Leu Gly Thr
  1               5                  10                  15

Ala Ile Leu Val Leu Phe Gly Asn Gly Ala Val Ala Asn Val Glu Leu
                 20                  25                  30

Lys Gly Thr Lys Gly Tyr Arg Asn Gly Trp Ile Ile Ala Ile Gly
         35                  40                  45

Tyr Gly Val Gly Val Met Leu Pro Ala Leu Met Phe Asn Lys Ile Ser
     50                  55                  60

Gly Ser Gln Thr Asn Pro Ala Met Thr Ile Gly Leu Ala Val Asn Gly
 65                  70                  75                  80

Leu Phe Pro Trp Ser Glu Val Ile Pro Tyr Ile Leu Ala Gln Phe Val
                 85                  90                  95

Gly Ala Ile Ile Gly Gln Val Ile Leu Tyr Phe Ile Tyr Leu Pro Phe
                100                 105                 110

Tyr Lys Gln Thr Glu Asp Thr Lys Ser Ile Leu Gly Thr Cys Ser Thr
            115                 120                 125

Ile Ser Ala Ser Gly Ser His Ile Asn Gly Phe Val Thr Glu Phe Phe
        130                 135                 140

Gly Thr Phe Leu Leu Val Leu Gly Ala Met Phe Ile Leu Asn Ser Thr
145                 150                 155                 160

Gly Val Lys Ser Thr Pro Ala Val Gly Tyr Val Gly Leu Gly Phe Leu
                165                 170                 175

Val Cys Ser Leu Val Ala Ser Leu Gly Gly Pro Thr Gly Pro Gly Leu
                180                 185                 190

Asn Pro Ala Arg Asp Leu Gly Pro Arg Ile Val His Ser Leu Leu Pro
            195                 200                 205
```

Leu Lys Asn Lys Gly Asn Ser Glu Trp Thr Tyr Ala Trp Ile Pro Val
    210                 215                 220

Leu Ala Pro Met Phe Gly Ser Ile Ile Ala Ile Phe Leu Phe Asn Lys
225                 230                 235                 240

Ile Tyr

<210> SEQ ID NO 22
<211> LENGTH: 729
<212> TYPE: DNA
<213> ORGANISM: Clostridium acetobutylicum

<400> SEQUENCE: 22

```
atgcattata gtttagctgt aaagttagtt tgcgaaatac ttggtacagc aattttagta    60
ctatttggta acggtgcagt tgctaatgta gaattaaaag gaactaaagg gtatcgcaat   120
ggctggatta ttattgccat tggttatggt gttggtgtaa tgcttccagc tttaatgttt   180
aataaaatta gtggtagtca gacaaatcca gctatgacaa taggattagc agtaaatggg   240
cttttttccgt ggtctgaggt tataccatat atattggctc agtttgtagg tgctataata   300
ggtcaagtta tctcttactt tatatacctt ccgtttttata aacaaacaga ggatactaaa   360
agcattcttg gtacatgttc tactatatca gcatcaggaa gtcatataaa tggatttgtc   420
acagaatttt ttggcacatt cttattggtt ttaggtgcaa tgtttattct taattcaact   480
ggagtaaaaa gtacacctgc agtaggttat gttggtcttg atttcttgt atgctcatta   540
gttgcatctt aggtggtcc aactggtcct ggattaaatc cagctagaga ttttgggccct   600
cgtatagtac attcactttt gccacttaaa aataaaggca attctgaatg gacatatgcc   660
tggattcctg ttttggcacc aatgtttgga agtattattg ctatattctt gtttaataaa   720
atatattaa                                                           729
```

<210> SEQ ID NO 23
<211> LENGTH: 336
<212> TYPE: PRT
<213> ORGANISM: Clostridium acetobutylicum

<400> SEQUENCE: 23

Met Asn Lys Ala Asp Tyr Lys Gly Val Trp Val Phe Ala Glu Gln Arg
1               5                   10                  15

Asp Gly Glu Leu Gln Lys Val Ser Leu Glu Leu Leu Gly Lys Gly Lys
                20                  25                  30

Glu Met Ala Glu Lys Leu Gly Val Glu Leu Thr Ala Val Leu Leu Gly
            35                  40                  45

His Asn Thr Glu Lys Met Ser Lys Asp Leu Leu Ser His Gly Ala Asp
        50                  55                  60

Lys Val Leu Ala Ala Asp Asn Glu Leu Leu Ala His Phe Ser Thr Asp
65                  70                  75                  80

Gly Tyr Ala Lys Val Ile Cys Asp Leu Val Asn Glu Arg Lys Pro Glu
                85                  90                  95

Ile Leu Phe Ile Gly Ala Thr Phe Ile Gly Arg Asp Leu Gly Pro Arg
            100                 105                 110

Ile Ala Ala Arg Leu Ser Thr Gly Leu Thr Ala Asp Cys Thr Ser Leu
        115                 120                 125

Asp Ile Asp Val Glu Asn Arg Asp Leu Leu Ala Thr Arg Pro Ala Phe
    130                 135                 140

Gly Gly Asn Leu Ile Ala Thr Ile Val Cys Ser Asp His Arg Pro Gln

```
                145                 150                 155                 160
Met Ala Thr Val Arg Pro Gly Val Phe Glu Lys Leu Pro Val Asn Asp
                    165                 170                 175

Ala Asn Val Ser Asp Asp Lys Ile Glu Lys Val Ala Ile Lys Leu Thr
                180                 185                 190

Ala Ser Asp Ile Arg Thr Lys Val Ser Lys Val Val Lys Leu Ala Lys
            195                 200                 205

Asp Ile Ala Asp Ile Gly Glu Ala Lys Val Leu Val Ala Gly Gly Arg
        210                 215                 220

Gly Val Gly Ser Lys Glu Asn Phe Glu Lys Leu Glu Glu Leu Ala Ser
225                 230                 235                 240

Leu Leu Gly Gly Thr Ile Ala Ala Ser Arg Ala Ala Ile Glu Lys Glu
                245                 250                 255

Trp Val Asp Lys Asp Leu Gln Val Gly Gln Thr Gly Lys Thr Val Arg
            260                 265                 270

Pro Thr Leu Tyr Ile Ala Cys Gly Ile Ser Gly Ala Ile Gln His Leu
        275                 280                 285

Ala Gly Met Gln Asp Ser Asp Tyr Ile Ile Ala Ile Asn Lys Asp Val
    290                 295                 300

Glu Ala Pro Ile Met Lys Val Ala Asp Leu Ala Ile Val Gly Asp Val
305                 310                 315                 320

Asn Lys Val Val Pro Glu Leu Ile Ala Gln Val Lys Ala Ala Asn Asn
                325                 330                 335

<210> SEQ ID NO 24
<211> LENGTH: 1011
<212> TYPE: DNA
<213> ORGANISM: Clostridium acetobutylicum

<400> SEQUENCE: 24
atgaataaag cagattacaa gggcgtatgg gtgtttgctg aacaaagaga cggagaatta      60
caaaaggtat cattggaatt attaggtaaa ggtaaggaaa tggctgagaa attaggcgtt     120
gaattaacag ctgttttact tggacataat actgaaaaaa tgtcaaagga tttattatct     180
catggagcag ataaggtttt agcagcagat aatgaacttt tagcacattt ttcaacagat     240
ggatatgcta agttatatg tgatttagtt aatgaaagaa agccagaaat attattcata     300
ggagctactt tcataggaag agatttagga ccaagaatag cagcaagact ttctactggt     360
ttaactgctg attgtacatc acttgacata gatgtagaaa atagagattt attggctaca     420
agaccagcgt ttggtggaaa tttgatagct acaatagttt gttcagacca cagaccacaa     480
atggctacag taagacctgg tgtgtttgaa aaattacctg ttaatgatgc aaatgtttct     540
gatgataaaa tagaaaaagt tgcaattaaa ttaacagcat cagacataag aacaaaagtt     600
tcaaaagttg ttaagcttgc taaagatatt gcagatatcg gagaagctaa ggtattagtt     660
gctggtggta gaggagttgg aagcaaagaa aactttgaaa aacttgaaga gttagcaagt     720
ttacttggtg gaacaatagc cgcttcaaga gcagcaatag aaaaagaatg ggttgataag     780
gaccttcaag taggtcaaac tggtaaaact gtaagaccaa ctctttatat tgcatgtggt     840
atatcaggag ctatccagca tttagcaggt atgcaagatt cagattacat aattgctata     900
aataaagatg tagaagcccc aataatgaag gtagcagatt tggctatagt tggtgatgta     960
aataaagttg taccagaatt aatagctcaa gttaaagctg ctaataatta a            1011

<210> SEQ ID NO 25
```

<211> LENGTH: 336
<212> TYPE: PRT
<213> ORGANISM: Clostridium acetobutylicum

<400> SEQUENCE: 25

```
Met Asn Lys Ala Asp Tyr Lys Gly Val Trp Val Phe Ala Glu Gln Arg
1               5                   10                  15

Asp Gly Glu Leu Gln Lys Val Ser Leu Glu Leu Leu Gly Lys Gly Lys
            20                  25                  30

Glu Met Ala Glu Lys Leu Gly Val Glu Leu Thr Ala Val Leu Leu Gly
        35                  40                  45

His Asn Thr Glu Lys Met Ser Lys Asp Leu Leu Ser His Gly Ala Asp
    50                  55                  60

Lys Val Leu Ala Ala Asp Asn Glu Leu Leu Ala His Phe Ser Thr Asp
65                  70                  75                  80

Gly Tyr Ala Lys Val Ile Cys Asp Leu Val Asn Glu Arg Lys Pro Glu
                85                  90                  95

Ile Leu Phe Ile Gly Ala Thr Phe Val Gly Arg Asp Leu Gly Pro Arg
            100                 105                 110

Ile Ala Ala Arg Leu Ser Thr Gly Leu Thr Ala Asp Cys Thr Ser Leu
        115                 120                 125

Asp Ile Asp Val Glu Asn Arg Asp Leu Leu Ala Thr Arg Pro Ala Phe
    130                 135                 140

Gly Gly Asn Leu Ile Ala Thr Ile Val Cys Ser Asp His Arg Pro Gln
145                 150                 155                 160

Met Ala Thr Val Arg Pro Gly Val Phe Glu Lys Leu Pro Val Asn Asp
                165                 170                 175

Ala Asn Val Ser Asp Asp Lys Ile Glu Lys Val Ala Ile Lys Leu Thr
            180                 185                 190

Ala Ser Asp Ile Arg Thr Lys Val Ser Lys Val Val Lys Leu Ala Lys
        195                 200                 205

Asp Ile Ala Asp Ile Gly Glu Ala Lys Val Leu Val Ala Gly Gly Arg
    210                 215                 220

Gly Val Gly Ser Lys Glu Asn Phe Glu Lys Leu Glu Glu Leu Ala Ser
225                 230                 235                 240

Leu Leu Gly Gly Thr Ile Ala Ala Ser Arg Ala Ala Ile Glu Lys Glu
                245                 250                 255

Trp Val Asp Lys Asp Leu Gln Val Gly Gln Thr Gly Lys Thr Val Arg
            260                 265                 270

Pro Thr Leu Tyr Ile Ala Cys Gly Ile Ser Gly Ala Ile Gln His Leu
        275                 280                 285

Ala Gly Met Gln Asp Ser Asp Tyr Ile Ile Ala Ile Asn Lys Asp Val
    290                 295                 300

Glu Ala Pro Ile Met Lys Val Ala Asp Leu Ala Ile Val Gly Asp Val
305                 310                 315                 320

Asn Lys Val Val Pro Glu Leu Ile Ala Gln Val Lys Ala Ala Asn Asn
                325                 330                 335
```

<210> SEQ ID NO 26
<211> LENGTH: 1011
<212> TYPE: DNA
<213> ORGANISM: Clostridium acetobutylicum

<400> SEQUENCE: 26
atgaataaag cagattacaa gggcgtatgg gtgtttgctg aacaaagaga cggagaatta     60

| | |
|---|---|
| caaaaggtat cattggaatt attaggtaaa ggtaaggaaa tggctgagaa attaggcgtt | 120 |
| gaattaacag ctgttttact tggacataat actgaaaaaa tgtcaaagga tttattatct | 180 |
| catggagcag ataaggtttt agcagcagat aatgaacttt agcacattt ttcaacagat | 240 |
| ggatatgcta aagttatatg tgatttagtt aatgaaagaa agccgaaat attattcata | 300 |
| ggagctactt tcgtaggaag agatttagga ccaagaatag cagcaagact ttctactggt | 360 |
| ttaactgctg attgtacatc acttgacata gatgtagaaa atagagattt attggctaca | 420 |
| agaccagcgt ttggtggaaa tttgatagct acaatagttt gttcagacca cagaccacaa | 480 |
| atggctacag taagacctgg tgtgtttgaa aaattacctg ttaatgatgc aaatgtttct | 540 |
| gatgataaaa tagaaaaagt tgcaattaaa ttaacagcat cagacataag aacaaaagtt | 600 |
| tcaaaagttg ttaagcttgc taaagatatt gcagatatcg gagaagctaa ggtattagtt | 660 |
| gctggtggta gaggagttgg aagcaaagaa acttttgaaa aacttgaaga gttagcaagt | 720 |
| ttacttggtg gaacaatagc cgcttcaaga gcagcaatag aaaaagaatg ggttgataag | 780 |
| gaccttcaag taggtcaaac tggtaaaact gtaagaccaa ctctttatat tgcatgtggt | 840 |
| atatcaggag ctatccagca tttagcaggt atgcaagatt cagattacat aattgctata | 900 |
| aataaagatg tagaagcccc aataatgaag gtagcagatt tggctatagt tggtgatgta | 960 |
| aataaagttg taccagaatt aatagctcaa gttaaagctg ctaataatta a | 1011 |

<210> SEQ ID NO 27
<211> LENGTH: 2364
<212> TYPE: DNA
<213> ORGANISM: Clostridium butyricum

<400> SEQUENCE: 27

| | |
|---|---|
| atgataagta aaggatttag tacccaaaca gaaagaataa atattttaaa ggctcaaata | 60 |
| ttaaatgcta aaccatgtgt tgaatcagaa agagcaatat taataacaga atcatttaaa | 120 |
| caaacagaag gccagccagc aattttaaga gagcattgg cattgaaaca catacttgaa | 180 |
| aatatcccta taacaattag agatcaagaa cttatagtgg aagtttaac taaagaacca | 240 |
| aggtcttcac aagtatttcc tgagttttct aataagtggt tacaagatga attggataga | 300 |
| ttaaataaga gaactggaga tgcattccaa atttcagaag aaagtaaaga aaaattaaaa | 360 |
| gatgtctttg agtattggaa tggaaagaca acaagtgagt tagcaacttc atatatgaca | 420 |
| gaggaaacaa gagaggcagt aaattgtgat gtatttactg taggaaacta ctattataat | 480 |
| ggcgtaggac atgtatctgt agattatgga aaagtattaa gggttggatt taatgggatt | 540 |
| ataaatgagg ctaaggaaca attagaaaaa acaggagta tagatcctga tttataaag | 600 |
| aaagaaaaat tcctaaatag tgttattatc tcatgcgaag ctgcaataac atatgtaaat | 660 |
| agatatgcta aaaaggctaa agagattgca gataatacaa gtgatgcaaa aagaaaagct | 720 |
| gaattaaatg aaatagcaaa aatttgttca aaagtttcag agagggagc taaatctttc | 780 |
| tatgaagcat gtcaattatt ttggtttatt catgcaataa taaatataga atctaatgga | 840 |
| cattctattt ctccagctag atttgatcaa tacatgtatc catattatga aaatgataaa | 900 |
| aatataacag ataagtttgc tcaagaatta atagattgta tctggattaa attaaatgat | 960 |
| attaataaag taagagatga gatttcaact aaacattttg gtggttaccc aatgtatcaa | 1020 |
| aacttaattg ttgggggtca aaattcagaa ggaaaagatg caactaataa agtatccatat | 1080 |
| atggcattag aagcagctgt ccatgtaaag ttgcctcagc catctttgtc agtaagaata | 1140 |
| tggaataaga ctccagatga attttttgctt agagcagcag aattaactag agaagggtta | 1200 |

```
ggacttcctg cttattataa tgatgaagtt attattccag cattagtttc tagaggtctt    1260
acattagaag atgcaagaga ctacggaata attggatgtg ttgaaccaca aaagccagga    1320
aaaacagaag gatggcatga ttcagcattc tttaatcttg caagaatagt agagttaact    1380
ataaattctg gatttgataa aaataaacag attggaccta aaactcaaaa ttttgaagaa    1440
atgaaatcct ttgatgaatt catgaaagct tataaagctc aaatggagta ttttgtaaaa    1500
catatgtgct gtgctgataa ttgcatagat attgcacatg cagaaagagc tccattacct    1560
ttcttgtcat caatggttga taattgtatc ggaaaaggaa agagccttca agatggtggt    1620
gcagaatata acttcagtgg accacaaggt gttggagtag ctaatattgg agattcatta    1680
gttgcagtta aaaaaattgt gtttgatgaa ataagatta ctccttcaga attaaagaaa    1740
acattaaata tgattttaa aaattcagaa gaaatacaag ccttactaaa aaatgctcct    1800
aagtttggaa atgatattga tgaagttgat aatttagcta gagagggtgc attagtatac    1860
tgtagagaag ttaataaata tacaaatcca aggggaggaa attttcaacc aggattatat    1920
ccatcttcaa ttaatgtata ttttggaagc ttaacaggtg ctactccaga tggaaggaaa    1980
tccggacaac cattagctga tggggtttct ccatcaagag ctgtgatgt atctggacct    2040 actgcagctt gtaactcagt tagtaaatta gatcatttta tagcttcaaa tggaacttta    2100
tttaatcaaa aattccatcc gtcagcatta aaggtgata atggattaat gaatttatca    2160
tcattaataa aagttatttt tgatcaaaag ggatttcatg ttcaatttaa tgtaatagat    2220
aaaaaaatat tacttgcagc acaaaaaaat cctgaaaaat atcaagattt aattgttaga    2280
gttgcaggat atagtgcaca gttcatttct ttagataaat ctattcaaaa tgatattatt    2340
gcaagaactg aacatgttat gtaa                                          2364
```

<210> SEQ ID NO 28
<211> LENGTH: 915
<212> TYPE: DNA
<213> ORGANISM: Clostridium butyricum

<400> SEQUENCE: 28

```
atgagtaagg agataaaagg cgttttattt aacatacaaa aattttcgtt acatgatggg      60
cctggaataa gaactatagt attttttaag ggatgttcaa tgtcgtgctt atggtgcagt     120
aatccagaat cccaagatat taaacctcaa gtaatgttta taaaaatttt atgtacaaaa     180
tgtggaagat gtaaatctca atgtaaaagt gcagctattg atatgaattc agaatatagg     240
atagataaaa gcaaatgtac agagtgtaca aaatgtgttg ataattgctt aagcggggca     300
cttgttattg aaggaaggaa ttacagtgtt gaagacgtta taaggaattt gaaaaaagat     360
agtgttcaat atagaagatc aaacggtgga attacactat ctggagggga agtattactt     420
caaccagatt ttgcagtgga gcttttaaaa gagtgtaaat catatggctg gcacactgcc     480
attgaaacag caatgtatgt taatagtgaa tctgtaaaaa aagtaattcc atatatagat     540
ctggctatga ttgatataaa agtatgaat gatgaaatcc ataggaaatt tacaggagtg     600
agtaacgaaa taatattca aaacattaaa ttaagtgatg aattagctaa gaaataata     660 atcagaattc ctgtaataga aggatttaat gcagatttac aaagtatagg agcaatagct     720
caattttcaa aatcattaac aaatcttaaa agaatagatc ttcttccata ccataattat     780
ggagaaaata gtatcaagc aattggaaga gagtattctt tgaaagaact aaaatcacct     840
agtaaagaca aaatggaaag attaaaagct ttagttgaaa tcatgggaat accgtgcaca     900
```

```
attggagctg agtaa                                              915
```

```
<210> SEQ ID NO 29
<211> LENGTH: 1158
<212> TYPE: DNA
<213> ORGANISM: Clostridium butyricum

<400> SEQUENCE: 29
atgagaatgt atgattattt agtaccaagt gtaaacttta tg

```
<212> TYPE: DNA
<213> ORGANISM: artificial
<220> FEATURE:
<223> OTHER INFORMATION: glpK oligo for Sanger sequencing

<400> SEQUENCE: 32
ggcaaagtcc atgtaaccg                                              19

<210> SEQ ID NO 33
<211> LENGTH: 33
<212> TYPE: DNA
<213> ORGANISM: artificial
<220> FEATURE:
<223> OTHER INFORMATION: hydA oligo for PCR reaction and for Sanger
      sequencing

<400> SEQUENCE: 33
catgttctat tgttactatg gaagaggtag tag                              33

<210> SEQ ID NO 34
<211> LENGTH: 29
<212> TYPE: DNA
<213> ORGANISM: artificial
<220> FEATURE:
<223> OTHER INFORMATION: hydA oligo for PCR reaction and for Sanger
      sequencing

<400> SEQUENCE: 34
gcagttatta taaatgctgc tactagagc                                   29

<210> SEQ ID NO 35
<211> LENGTH: 31
<212> TYPE: DNA
<213> ORGANISM: artificial
<220> FEATURE:
<223> OTHER INFORMATION: hydA oligo for Sanger sequencing

<400> SEQUENCE: 35
cgtgaggttg acctccacca tttatacatc c                                31

<210> SEQ ID NO 36
<211> LENGTH: 21
<212> TYPE: DNA
<213> ORGANISM: artificial
<220> FEATURE:
<223> OTHER INFORMATION: hydA oligo for Sanger sequencing

<400> SEQUENCE: 36
gtggacaatg ttctagaaga g                                           21

<210> SEQ ID NO 37
<211> LENGTH: 19
<212> TYPE: DNA
<213> ORGANISM: artificial
<220> FEATURE:
<223> OTHER INFORMATION: glpF oligo for PCR reaction

<400> SEQUENCE: 37
atgcattata gtttagctg                                              19

<210> SEQ ID NO 38
<211> LENGTH: 20
<212> TYPE: DNA
<213> ORGANISM: artificial
<220> FEATURE:
<223> OTHER INFORMATION: glpF oligo for PCR reaction and for Sanger
      sequencing
```

```
<400> SEQUENCE: 38
cgtatttatg ttaacacagg                                             20

<210> SEQ ID NO 39
<211> LENGTH: 22
<212> TYPE: DNA
<213> ORGANISM: artificial
<220> FEATURE:
<223> OTHER INFORMATION: glpF oligo for Sanger sequencing

<400> SEQUENCE: 39
ctgtgacaaa tccatttata tg                                          22

<210> SEQ ID NO 40
<211> LENGTH: 22
<212> TYPE: DNA
<213> ORGANISM: artificial
<220> FEATURE:
<223> OTHER INFORMATION: etfA oligo for PCR reaction and for Sanger
      sequencing

<400> SEQUENCE: 40
gaagttaaag gacagggaga ag                                          22

<210> SEQ ID NO 41
<211> LENGTH: 20
<212> TYPE: DNA
<213> ORGANISM: artificial
<220> FEATURE:
<223> OTHER INFORMATION: etfA oligo for PCR reaction and for Sanger
      sequencing

<400> SEQUENCE: 41
gcaaatgcct gagcaattcc                                             20

<210> SEQ ID NO 42
<211> LENGTH: 19
<212> TYPE: DNA
<213> ORGANISM: artificial
<220> FEATURE:
<223> OTHER INFORMATION: gapC primer F

<400> SEQUENCE: 42
tgctgctgta agtatcatc                                              19

<210> SEQ ID NO 43
<211> LENGTH: 18
<212> TYPE: DNA
<213> ORGANISM: artificial
<220> FEATURE:
<223> OTHER INFORMATION: gapC primer R

<400> SEQUENCE: 43
gttggaactg gaactctt                                               18

<210> SEQ ID NO 44
<211> LENGTH: 19
<212> TYPE: DNA
<213> ORGANISM: artificial
<220> FEATURE:
<223> OTHER INFORMATION: cpn60 primer F

<400> SEQUENCE: 44
ttatatgtgc accgatatg                                              19
```

-continued

```
<210> SEQ ID NO 45
<211> LENGTH: 19
<212> TYPE: DNA
<213> ORGANISM: artificial
<220> FEATURE:
<223> OTHER INFORMATION: cpn60 primer R

<400> SEQUENCE: 45
gagaagtctt gcgccggac                                                19

<210> SEQ ID NO 46
<211> LENGTH: 18
<212> TYPE: DNA
<213> ORGANISM: artificial
<220> FEATURE:
<223> OTHER INFORMATION: tpi primer F

<400> SEQUENCE: 46
ccagcggtat tagaagaa                                                 18

<210> SEQ ID NO 47
<211> LENGTH: 24
<212> TYPE: DNA
<213> ORGANISM: artificial
<220> FEATURE:
<223> OTHER INFORMATION: tpi primer R

<400> SEQUENCE: 47
gtcctataat tacataatga actc                                          24
```

MICROORGANISMS WITH IMPROVED 1,3-PROPANEDIOL AND BUTYRIC ACID PRODUCTION

The present invention concerns a new mutant strain of *Clostridium acetobutylicum* able to produce 1,3-propanediol and comprising attenuated glycerol kinase activity. In addition, the present invention concerns a consortium of *Clostridium* species comprising at least said mutant strain and at least one other Clostridia chosen among *C. sporogenes* and *C. sphenoides*. This modified strain may be adapted for growth and for the production of 1,3-propanediol in an appropriate culture medium with high glycerol content. The invention also relates to a method for the production of 1,3-propanediol and butyric acid, by culturing at least this mutant strain in an appropriate culture medium.

BACKGROUND OF THE INVENTION 1,3-propanediol (PDO), also called trimethylene glycol or propylene glycol, is one of the oldest known fermentation products. It was originally identified as early as 1881 by August Freund in a glycerine fermented culture containing *Clostridium pasteurianum*. PDO is a typical product of glycerine fermentation and has been found in anaerobic conversions of other organic substrates. Only very few organisms, all of them bacteria, are able to form it. They include bacteria of the genera *Klebsiella* (*K. pneumoniae*), *Enterobacter* (*E. agglomerans*), *Citrobacter* (*C. freundii*), Lactobacilli (*L. brevis* and *L. buchneri*) and Clostridia of the *C. butyricum* and the *C. pasteurianum* group.

PDO, as a bifunctional organic compound, may potentially be used for many synthesis reactions, in particular as a monomer for polycondensations to produce polyesters, polyethers, polyurethanes, and in particular, polytrimethylene terephtalate (PTT). These structure and reactivity features lead to several applications in cosmetics, textiles (clothing fibers or flooring) or plastics (car industry and packing or coating).

PDO can be produced by different chemical routes but they generate waste stream containing extremely polluting substances and the cost of production is high. Thus, chemically produced PDO cannot compete with the petrochemically available diols like 1,2-ethanediol, 1,2-propanediol and 1,4-butanediol. To increase this competitiveness, in 1995, DuPont started a research program for the biological conversion of glucose to PDO. Although this process is environmentally friendly it has the disadvantage to i) use vitamin B12, a very expensive cofactor and ii) be a discontinuous process due to the instability of the producing strain.

Due to the availability of large amounts of glycerol produced by the bio-diesel industry, a continuous, vitamin-B12-free process with a higher carbon yield would on the contrary, be advantageous.

It is known in the art that PDO can be produced from glycerine, an unwanted by-product in particular from the biodiesel production that contains roughly 80-85% of glycerol mixed with salts and water.

*C. butyricum* was previously described as being able to grow and produce PDO from glycerol contained in industrial glycerine in batch and two-stage continuous fermentation (Papanikolaou et al., 2000). However, at the highest glycerol concentration, the maximal PDO titer obtained was 48.1 $g \cdot L^{-1}$ at a dilution rate of 0.02 $h^{-1}$, meaning a productivity of 0.96 $g \cdot L^{-1} \cdot h^{-1}$. The cultures were conducted with a maximum concentration of glycerol originating from glycerine in the fed medium of 90 $g \cdot L^{-1}$ and in the presence of yeast extract, a costly compound containing organic nitrogen that is known by the man skilled in the art to help increase bacterial biomass production.

Application WO 2006/128381 discloses the use of this glycerol for the production of PDO with batch and fed-batch cultures using natural PDO producing organisms such as *Klebsiella pneumoniae, C. butyricum* or *C. pasteurianum*. Furthermore, the medium used in WO 2006/128381 also contains yeast extract. As described in this patent application, the maximal productivity reached was comprised between 0.8 and 1.1 $g \cdot l^{-1} \cdot h^{-1}$.

The performance of a *C. acetobutylicum* strain modified to contain the vitamin B12-independent glycerine-dehydratase and the PDO-dehydrogenase from *C. butyricum*, called "*C. acetobutylicum* DG1 pSPD5" strain has been described in Gonzalez-Pajuelo et al., 2005. This strain originally grows and produces PDO in a fed medium containing up to 120 $g \cdot l^{-1}$ of pure glycerol. In addition, analyses in a fed medium containing a maximum of 60 $g \cdot l^{-1}$ of pure glycerol or glycerol contained in industrial glycerine did not point out to any differences. These results have been obtained in presence of yeast extract. Moreover, no test was performed with concentrations of glycerol originating from industrial glycerine higher than 60 $g \cdot l^{-1}$. When comparing a wild-type *C. butyricum* to the modified microorganism "*C. acetobutylicum* DG1 pSPD5", a globally similar behaviour was observed.

In patent application WO 2010/128070 the inventors described a process to adapt the strain of *C. acetobutylicum* DG1 pSPD5 such as described in Gonzalez-Pajuelo et al. (2005) to grow in a medium with a high concentration of glycerol contained in industrial glycerine and without yeast extract. The resulting population of *C. acetobutylicum* DG1 pSPD5 adapted strains was able to produce PDO in medium containing up to 120 $g \cdot l^{-1}$ of glycerol contained in industrial glycerine with a titer up to 53.5 $g \cdot L^{-1}$ of PDO, a yield up to 0.53 $g \cdot g^{-1}$ and productivity up to 2.86 $g \cdot L^{-1} \cdot h^{-1}$. In patent application WO 2012/062832, the inventors described the isolation of clone from another population of *C. acetobutylicum* DG1 pSPD5 adapted strains obtained by the same process as described in WO 2010/128070 patent application. This second population was able to produce PDO in medium containing around 105 $g \cdot L^{-1}$ of glycerol contained in industrial glycerine with a titer up to 50.45 $g/L^{-1}$ of PDO, a yield up to 0.53 $g \cdot g^{-1}$ and productivity up to 3.18 $g \cdot L^{-1} \cdot h^{-1}$ whereas isolated clone was able to produce PDO in medium containing around 105 $g \cdot L^{-1}$ of glycerol contained in industrial glycerine with a titer up to 51.30 $g/L^{-1}$ of PDO, a yield up to 0.50 $g \cdot g^{-1}$ and productivity up to 3.05 $g \cdot L^{-1} \cdot h^{-1}$.

Butyrate (also named Butyric Acid or butanoic acid, abbreviated BA) is a carboxylic acid with the structural formula $CH_3CH_2CH_2$—COOH, which is volatile, colourless, oily liquid with an unpleasant odour, miscible in both water and solvents, such as ethanol and ether. Butyrate is used for a variety of applications including i) the fabrication of other chemicals, ii) as feed additive in animal nutrition iii) as a food flavouring, or food supplement, and iv) in pharmaceutical and cosmetic compositions. In particular, butyrate may be used as a feedstock in the production of thermoplastic polymers, such as cellulose acetate butyrate, one of the most commercially important mixed esters. Indeed, cellulose acetate butyrate is often present in paints and polymers. Butyrate is also a precursor to butanol, a biofuel and possible gasoline replacement for internal combustion.

Currently, production of butyrate on an industrial scale is mainly performed using chemical synthesis, for example via the oxidation of n-butyl alcohol or butyraldehyde with oxygen or organic oxidants. Alternatively, butyrate may be produced by extraction from butter, which contains an estimated 2-4% of butyrate, though this method is costly and difficult. Butyrate may also be produced as a metabolite in *Clostridium* strains during fermentation under anaerobic conditions. More specifically, butyrate may be produced as an acetate/butyrate mixture, which is an intermediate in biphasic acetone/n-butanol/ethanol (ABE) fermentation. Production of acetate/butyrate occurs in the first acidogenic phase under high growth rate conditions, and is then consumed in the second solventogenic phase, in which growth rate decreases and ABE solvents are produced. Carbon dioxide and hydrogen are produced throughout the fermentation process.

In the present patent application, the inventors have noticed that a strain of *Clostridium acetobutylicum* DG1 pSPD5 able to produce PDO in presence of glycerol mutated for having an attenuated glycerol kinase activity provides an improved production of PDO and BA compared to the performances of a non-mutated producer strain. Further improvement of production of PDO and BA may be obtained when the mutant strain according to the invention is further carrying an attenuated hydrogene dehydrogenase activity and/or an enhanced glycerol uptake facilitator permease activity.

Thus, using the mutant strain of *Clostridium* according to the invention conducts to an improved production of PDO and BA, compared with using a non-mutated *C. acetobutylicum* DG1 pSPD5 strain just adapted for producing PDO in presence of glycerol.

BRIEF DESCRIPTION OF THE INVENTION

The present invention concerns a mutant strain of *Clostridium acetobutylicum* expressing the dhaB1, dhaB2 and dhaT genes from *C. butyricum* and comprising attenuated glycerol kinase activity.

Particularly, in the mutant stain according to the present invention, the glycerol kinase whose activity is attenuated is encoded by the gene glpK at locus CA_C1321 in the *C. acetobutylicum* genome ATCC824.

In a particular embodiment of the invention, the mutant strain according to the invention comprises at least one of the following mutations in the gene glpK at locus CA_C1321:
  a. Mutation of the codon at nucleotide positions 1462461 to 1462463 in the *C. acetobutylicum* genome ATCC824, Genbank AE001437, for having amino acid alanine in position 347 to be replaced with threonine,
  b. Mutation of the codon at nucleotide positions 1461486 to 1461488 in the *C. acetobutylicum* genome ATCC824, Genbank AE001437, for having amino acid histidine in position 22 to be replaced with tyrosine,
  c. Mutation of the codon at nucleotide positions 1462818 to 1462820 in the *C. acetobutylicum* genome ATCC824, Genbank AE001437, for having amino acid valine in position 466 to be replaced by methionine In a preferred embodiment of the invention, the mutant strain according to the invention comprises the combination of the three mutations.

The mutant strain of the invention may also further comprise attenuated hydrogen dehydrogenase activity, preferably inactivated hydrogen dehydrogenase activity. In a particular embodiment of the invention, said hydrogenase is encoded by the gene hydA at locus CA_C0028 in the *C. acetobutylicum* genome ATCC824, Genbank AE001437.

The mutant strain of the invention may also further comprise enhanced glycerol uptake facilitator permease activity. In a particular embodiment of the invention, said glycerol uptake facilitator protein is encoded by the gene glpF at locus CA_C0770 in the *C. acetobutylicum* genome ATCC824, Genbank AE001437.

The mutant strain of the invention may also further comprise attenuated electron transfer flavoprotein subunit alpha activity. In a particular embodiment of the invention, said electron transfer flavoprotein subunit alpha is encoded by the gene etfA at locus CA_C2709 in the *C. acetobutylicum* genome ATCC824, Genbank AE001437.

The present invention also concerns a consortium of Clostridia species comprising the mutant strain of *C. acetobutylicum* according to the invention as disclosed above.

In a particular embodiment of the invention, this consortium comprises the mutant strain *Clostridium acetobutylicum* as defined above and at least one strain of *Clostridium sporogenes* and/or at least one strain of *Clostridium sphenoides*.

The present invention also concerns a method for the production of PDO and BA comprising culturing the mutant strain *Clostridium acetobutylicum* or a consortium comprising said mutant strain as defined above, in an appropriate culture medium comprising at least glycerine and recovering the PDO and/or BA produced from the culture medium.

DETAILED DESCRIPTION OF THE INVENTION

In a first aspect, the present invention concerns a mutant strain of *Clostridium acetobutylicum* able to produce PDO and comprising attenuated glycerol kinase activity, compared to a non-mutated strain. In the present invention, a glycerol kinase is an enzyme also named ATP:glycerol 3-phosphotransferase or glycerokinase GK.

Particularly, in the mutant strain according to the present invention, the glycerol kinase (SEQ ID NO: 1) whose activity is attenuated is encoded by the gene glpK at locus CA_C1321 (SEQ ID NO: 2) in the *C. acetobutylicum* genome ATCC824. In the mutant strain according to the present invention, the glycerol kinase activity is attenuated compared to a non-mutated strain, in particular compared to a strain in which the gene glpK is not mutated.

As mentioned herein, the *C. acetobutylicum* genome ATCC824 corresponds to the 3940880 bp circular DNA available under the access number Genbank AE001437 (AE007513-AE007868), version AE001437.1 as *Clostridium acetobutylicum* ATCC 824, complete genome.

In a particular embodiment of the invention, the mutant strain according to the invention comprises at least one of the following mutations in the gene glpK at locus CA_C1321.
  a. Mutation of the codon at nucleotide positions 1462461 to 1462463 in the *C. acetobutylicum* genome ATCC824, Genbank AE001437, for having amino acid alanine in position 347 to be replaced with threonine, leading to a mutated protein with SEQ ID NO: SEQ ID NO: 3 and mutated gene with SEQ ID NO: 4,
  b. Mutation of the codon at nucleotide positions 1461486 to 1461488 in the *C. acetobutylicum* genome ATCC824, Genbank AE001437, for having amino acid histidine in position 22 to be replaced with tyrosine, leading to a mutated protein with SEQ ID NO: 5 and mutated gene with SEQ ID NO: 6,
  c. Mutation of the codon at nucleotide positions 1462818 to 1462820 in the *C. acetobutylicum* genome ATCC824, Genbank AE001437, for having amino acid valine in position 466 to be replaced by methionine, leading to a mutated protein with SEQ ID NO: 7 and mutated gene with SEQ ID NO: 8.

In an advantageous embodiment of the present invention, the mutant strain comprises at locus CA_C1321, at least mutation of the codon at nucleotide positions 1462461 to 1462463 in the *C. acetobutylicum* genome ATCC824, Genbank AE001437, for having amino acid alanine in position 347 to be replaced with threonine (SEQ ID NO: 3 and SEQ ID NO: 4).

In a preferred embodiment of the present invention, the mutant strain comprises at locus CA_C1321, at least:
(i) mutation of the codon at nucleotide positions 1462461 to 1462463 in the *C. acetobutylicum* genome ATCC824, Genbank AE001437, for having amino acid alanine in position 347 to be replaced with threonine, and
(ii) mutation of the codon at nucleotide positions 1461486 to 1461488 in the *C. acetobutylicum* genome ATCC824, Genbank AE001437, for having amino acid histidine in position 22 is to be replaced by with tyrosine,
leading to the mutated protein with SEQ ID NO: 9 and to the mutated gene with SEQ ID NO: 10.

In another preferred embodiment of the present invention, the mutant strain comprises at locus CA_C1321, at least:
(i) mutation of the codon at nucleotide positions 1462461 to 1462463 in the *C. acetobutylicum* genome ATCC824, Genbank AE001437, for having amino acid alanine in position 347 to be replaced with threonine, and
(ii) mutation of the codon at nucleotide positions 1462818 to 1462820 in the *C. acetobutylicum* genome ATCC824, Genbank AE001437, for having amino acid valine in position 466 to be replaced by methionine,
leading to the mutated protein with SEQ ID NO: 11 and to the mutated gene with SEQ ID NO: 12.

In another preferred embodiment of the present invention, the mutant strain comprises at locus CA_C1321, at least:
(i) mutation of the codon at nucleotide positions 1462461 to 1462463 in the *C. acetobutylicum* genome ATCC824, Genbank AE001437, for having amino acid alanine in position 347 to be replaced with threonine, and
(ii) mutation of the codon at nucleotide positions 1461486 to 1461488 in the *C. acetobutylicum* genome ATCC824, Genbank AE001437, for having amino acid histidine in position 22 is to be replaced by with tyrosine, and
(iii) mutation of the codon at nucleotide positions 1462818 to 1462820 in the *C. acetobutylicum* genome ATCC824, Genbank AE001437, for having amino acid valine in position 466 to be replaced by methionine,
leading to the mutated protein with SEQ ID NO: 13 and to the mutated gene with SEQ ID NO: 14.

In all the above-mentioned particular and preferred embodiments, each of the mutation are preferably the following:
G replaced with A, at nucleotide position 1462461 in the *C. acetobutylicum* genome ATCC824, Genbank AE001437,
C replaced with T at nucleotide position 1461486 in the *C. acetobutylicum* genome ATCC824, Genbank AE001437;
G replaced with A at nucleotide position 1462818 in the *C. acetobutylicum* genome ATCC824, Genbank AE001437.

The mutant strain of the invention may also further comprise attenuated hydrogen dehydrogenase activity, preferably inactivated hydrogen dehydrogenase activity. In a particular embodiment of the invention, said hydrogenase (SEQ ID NO: 15) is encoded by the gene hydA (SEQ ID NO: 16) at locus CA_C0028 in the *C. acetobutylicum* genome ATCC824, Genbank AE001437.

In a preferred embodiment of the present invention, the mutant strain comprises at locus CA_C0028, at least mutation of the codon at nucleotide positions 39233 to 39235 in the *C. acetobutylicum* genome ATCC824, Genbank AE001437, for having a stop codon leading to a shorter protein of 209 amino acids instead of 582 amino acid of SEQ ID NO: 17, preferably by deletion of C at nucleotide position 39233 (mutated gene of SEQ ID NO: 18).

The mutant strain of the invention may also further comprise enhanced glycerol uptake facilitator permease activity. In a particular embodiment of the invention, said glycerol uptake facilitator protein (SEQ ID NO: 19) is encoded by the gene glpF (SEQ ID NO: 20) at locus CA_C0770 in the *C. acetobutylicum* genome ATCC824, Genbank AE001437.

In a preferred embodiment of the present invention, the mutant strain comprises at locus CA_C0770, at least mutation of the codon at nucleotide positions 892875 to 892877 in the *C. acetobutylicum* genome ATCC824, Genbank AE001437, for having amino acid methionine in position 13 to be replaced with isoleucine (mutated protein of SEQ ID NO: 21), preferably by replacement of G at nucleotide position 892875 with A, C or T, more preferably with A (mutated gene of SEQ ID NO: 22).

The mutant strain of the invention may also further comprise attenuated electron transfer flavoprotein subunit alpha activity. In a particular embodiment of the invention, said electron transfer flavoprotein subunit alpha (SEQ ID NO: 23) is encoded by the gene etfA (SEQ ID NO: 24) at locus CA_C2709 in the *C. acetobutylicum* genome ATCC824, Genbank AE001437.

In a preferred embodiment of the present invention, the mutant strain comprises at locus CA_C2709, at least mutation of the codon at nucleotide positions 2833384 to 2833386 in the *C. acetobutylicum* genome ATCC824, Genbank AE001437, for having amino acid isoleucine in position 105 to be replaced with valine (mutated protein of SEQ ID NO: 25), preferably by replacement of A at nucleotide position 2833384 with G (mutated gene of SEQ ID NO: 26).

The mutant strain *C. acetobutylicum* according to the present invention is modified to be able to produce 1,3-propanediol when culturing in an appropriate culture medium in presence of glycerol. This mutant *C. acetobutylicum* strain is modified to contain the 1,3-propanediol operon from *C. butyricum*: the vitamin B12-independent glycerol-dehydratase encoded by dhaB1 (SEQ ID NO: 27) and dhaB2 (SEQ ID NO: 28) genes and the PDO-dehydrogenase encoded by dhaT (SEQ ID NO: 29) gene by introducing extra copies of the 1,3-propanediol operon from *C. butyricum* either over-expressed by a plasmid or integrated into the chromosome of the microorganism. For example, the pSPD5 plasmid can be used for an over-expression of the 1,3-propanediol operon. This mutant *C. acetobutylicum* strain is called *C. acetobutylicum* DG1 pSPD5 and has been fully described in Gonzalez-Pajuelo et al., 2005 and in Gonzalez-Pajuelo et al., 2006 which are incorporated herein by reference.

Method for directing the glycerol metabolism towards production of PDO are known in the art (see for instance WO 2006/128381, Gonzalez-Pajuelo et al., 2006). Also as for example, strains of *C. acetobutylicum* genetically modified for the production of PDO from glycerol as sole source of carbon are known in the art and disclosed, particularly in applications WO 2001/04324 and WO 2010/128070.

In an advantageous embodiment, the mutant strain of the present invention is a strain *C. acetobutylicum* which is adapted for growth and production of PDO from a culture medium with high glycerol content and specifically with a high concentration of glycerol contained in industrial glycerine and without any organic nitrogen source.

A "*C. acetobutylicum* adapted", "*C. acetobutylicum* previously adapted", or "*C. acetobutylicum* being adapted" means a *C. acetobutylicum* which is modified to be able to grow on high concentration of industrial glycerine.

For example, the *C. acetobutylicum* strain may be adapted to grow in a culture medium with high glycerol content and specifically with a high concentration of glycerol originating from industrial glycerine by a selection pressure culturing process as disclosed in WO 2010/128070 patent application. The adaptation of the strain *C. acetobutylicum* is preferably carried out by an anaerobic continuous process which is a technique well known by the skilled person. Among the particulars of this process known by the one skilled in the art, it may be for example mentioned that fed medium is added to the fermenter continuously and an equivalent amount of converted nutrient solution with microorganisms is simultaneously removed from the system. The rate of nutrient exchange is expressed as the dilution rate. Hence the dilution rate is applied to the culture medium, takes into consideration maximum growth rate of the microorganism and impacts the rate of intake and withdrawal of the medium. Said adaptation of the producing microorganism is obtained by culturing the microorganism on a culture medium comprising high industrial glycerine content (comprised between 90 and 120 g/L, and preferably of about 105 g/L) at a low dilution rate (comprised between 0.005 and 0.1 $h^{-1}$, preferably between 0.005 and 0.02 $h^{-1}$), and selecting the adapted microorganism able to grow on the culture medium having high concentration of glycerol originating from industrial glycerine.

The expression "genetically modified" means that the strain has been transformed in the aim to change its genetic characteristics. Endogenous genes can be attenuated, deleted, or over-expressed, or preferably exogenous genes can be introduced, carried by a plasmid, or integrated into the genome of the strain, to be expressed into the cell.

The term "plasmid" or "vector" as used herein refers to an extra chromosomal element often carrying genes which are not part of the central metabolism of the cell, and usually in the form of circular double-stranded DNA molecules.

Any standard techniques of mutagenesis and/or gene replacement in *Clostridium*, such as disclosed in application WO 2008/040387 which contents are incorporated herein by reference, may be used for adapting the *C. acetobutylicum* strain for growth and production of 1,3-propanediol from a culture medium with high glycerol content and specifically with a high concentration of glycerol originating from industrial glycerine.

The man skilled in the art knows how to manage each of these experimental conditions, and to define the culture conditions for the Clostridia strains used according to the invention. In particular Clostridia strains are fermented at a temperature between 20° C. and 60° C., preferentially between 25° C. and 40° C. for *C. acetobutylicum*.

The activity of each enzyme mentioned herein which is modified in the mutant strain of the invention is intended to mean the specific activity.

In addition, the activity of each enzyme which is modified in the mutant strain of the invention is defined compared to a non-mutated strain or wild-type strain of *Clostridium acetobutylicum*.

The terms "enhanced", "expressing," "overexpressing," or "overexpression" of a protein of interest, such as an enzyme, refer herein to a significant increase in the expression level and/or activity of said protein in a microorganism, as compared to the parent microorganism in which the expression level and/or activity of said protein of interest is not modified, especially not genetically modified. In contrast, the terms "attenuated", "attenuating" or "attenuation" of a protein of interest refer to a significant decrease in the expression level and/or activity of said protein in a microorganism, as compared to the parent microorganism in which the expression level and/or activity of said protein of interest is not modified, especially not genetically modified. The complete attenuation of the expression level and/or activity of a protein of interest means that expression and/or activity is abolished; thus, the expression level of said protein is null. Where the "enhanced", "expressing," "over-expressing,", "overexpression" "attenuated", "attenuating" or "attenuation" is/are due to a mutation in the corresponding gene or protein of interest, the modification of the expression level and/or activity of said gene or protein of interest is compared to the expression level and/or activity of the same non-mutated gene or protein of interest.

The term "expression level", as applied herein, refers to the amount (e.g. relative amount, concentration) of a protein of interest (or of the gene encoding said protein) expressed in a microorganism, which is measurable by methods well-known in the art, such as by Western Blot-Immunoblot (Burnette, 1981), Enzyme-linked immunosorbent assay (e.g. ELISA) (Engvall and Perlman, 1971), or quantitative proteomics (Bantscheff et al., 2007).

Modulating the expression level of one or more proteins may occur by altering the expression of one or more endogenous genes that encode said protein within the microorganism.

Thus, in addition to the mutations, especially to the specific mutations disclosed above for modulating the glpK gene expression, the hydA gene expression, the etfA gene, and/or the gene glpF, classical means well known by the skilled person in the art may be used for further attenuating, abolishing or overexpressing the gene expression of the above-mentioned enzyme as described above in the mutant strain of the invention.

The expression level of endogenous genes coding for enzymes having a particular activity can notably be over-expressed, attenuated, or abolished in the recombinant microorganism according to the invention. Such modifications can be performed, for example, by genetic engineering, by adaptation, wherein a microorganism is cultured in that apply a specific stress on the microorganism and induce mutagenesis, and/or by forcing the development and evolution of metabolic pathways by combining directed mutagenesis and evolution under specific selection pressure.

The term "endogenous gene" refers herein to a gene that is naturally present in a microorganism.

An endogenous gene can notably be overexpressed or attenuated by introducing heterologous sequences which favor upregulation or downregulation, respectively, in addition to endogenous regulatory elements. Additionally, or alternatively, endogenous regulatory elements may themselves be replaced with appropriate heterologous sequences modulating gene expression. Additionally, or alternatively, one or more supplementary copies of the endogenous gene may be introduced chromosomally (i.e. into the chromosome) or extra-chromosomally (e.g. into a plasmid or vector) within the microorganism. Thus, the microorganism comprises several copies of a gene that are homologous to one another. When one or more supplementary copies of the endogenous gene are expressed extra-chromosomally, they may be carried on different types of plasmid, as detailed above for the introduction of extra-chromosomal exogenous genes.

Another way to overexpress or attenuate the expression of an endogenous gene is to exchange its promoter (i.e. wild-type promoter) with a stronger or weaker promoter, respectively. Promoters suitable for such purposes may be homologous (i.e. originating from the same species) or heterologous (i.e. originating from a different species), and are well known in the art. Indeed, the skilled person can easily select an appropriate promoter for modulating the expression of an endogenous gene.

Endogenous gene expression levels, or the activity of the encoded protein, can also be increased or attenuated by introducing mutations into the coding sequence of a gene or into non-coding sequences. These mutations may be synonymous, when no modification in the corresponding amino acid occurs, or non-synonymous, when the corresponding amino acid is altered. Synonymous mutations do not have any impact on the function of translated proteins but may have an impact on the regulation of the corresponding genes or even of other genes, if the mutated sequence is located in a binding site for a regulator factor. Non-synonymous mutations may have an impact on the function or activity of the translated protein as well as on regulation depending the nature of the mutated sequence. In particular, mutations in non-coding sequences may be located upstream of the coding sequence (i.e. in the promoter region, in an enhancer, silencer, or insulator region, in a specific transcription factor binding site) or downstream of the coding sequence. Mutations introduced in the promoter region may be in the core promoter, proximal promoter or distal promoter. Mutations may be introduced by site-directed mutagenesis using, for example, Polymerase Chain Reaction (PCR), by random mutagenesis techniques for example via mutagenic agents (Ultra-Violet rays or chemical agents like nitrosoguanidine (NTG) or ethylmethanesulfonate (EMS)) or DNA shuffling or error-prone PCR or using culture conditions that apply a specific stress on the microorganism and induce mutagenesis. The insertion of one or more supplementary nucleotide in the region located upstream of a gene can notably modulate gene expression.

In a second aspect, the present invention concerns a consortium of Clostridia comprising the PDO and BA producing mutant strain according to the invention as disclosed above.

In a particular embodiment of the invention, this consortium comprises the mutant strain *Clostridium acetobutylicum* as defined above and at least one strain of *Clostridium sporogenes* and/or at least one strain of *Clostridium sphenoides*.

Preferably, the consortium according to the present invention comprises from 89 to 98% of *C. acetobutylicum*, from 1% to 10% of *C. sporogenes*, and/or from 1% to 10 of *C. sphenoides* considering that the totality of the cells contained in the culture corresponds to 100%. More preferably, the consortium according to the present invention comprises from 89% to 95% of *C. acetobutylicum*, from 3% to 7% of *C. sporogenes*, and/or from 1% to 5% of *C. sphenoides* considering that the totality of the cells contained in the culture corresponds to 100%.

The consortium according to the present invention preferably comprises the PDO and BA producing mutant strain *C. acetobutylicum* which is previously modified for growth and production of PDO from a culture medium in presence of glycerol. All the preferred embodiment concerning the mutant strain *C. acetobutylicum* mentioned above also apply mutatis mutandis to this specific embodiment.

In a third aspect, the present invention concerns a method for the production of PDO and BA comprising culturing the mutant strain *Clostridium acetobutylicum* or a consortium comprising said mutant strain as defined above, in an appropriate culture medium comprising at least glycerol and recovering the PDO and/or the BA produced from the culture medium.

In the methods of the invention, the production is advantageously done in a batch, fed-batch or continuous process. Culturing microorganisms at industrial scale for the production of PDO and BA is known in the art, particularly disclosed in WO2010/128070 and WO2011/042434, which content are incorporated herein by reference.

In the methods according to the invention, the PDO and/or BA obtained, may be further purified after recovering.

Methods for recovering and eventually purifying PDO or BA from a fermentation medium are known to the skilled person. PDO may be isolated by distillation. In most embodiments, PDO is distilled from the fermentation medium with a by-product, such as acetate, and then further purified by known methods. A particular purification method is disclosed in applications WO2009/068110 and WO 2010/037843, which content is incorporated herein by reference.

BA may be isolated by distillation as disclosed in patent application EP350355 or by liquid-liquid extraction as disclosed for instance in WO2017/013335 using solvent preferably chosen among carboxylic acid such as pentanoic acid, hexanoic acid, heptanoic acid, octanoic acid or nonanoic acid or ketone such as methyl isobutyl ketone, methyl isoamyl ketone, methyl heptyl ketone, methyl nonyl ketone.

In a preferred embodiment of the method for the production of PDO and BA according to the present invention, glycerol concentration is from 90 to 120 g/L in the culture medium, preferably about 105 g/L.

An "appropriate culture medium" or a "culture medium" refers to a culture medium optimized for the growth of the *Clostridium* strains or consortium and the synthesis of product of interest by the cells. The fermentation process is generally conducted in reactors with a synthetic, particularly inorganic, culture medium of known defined composition adapted to the *Clostridium* species used and containing glycerol.

The term "synthetic medium" means a culture medium comprising a chemically defined composition on which organisms are grown. In the culture medium of the present invention, glycerol is advantageously the single source of carbon. Nevertheless, the culture medium may comprise a carbohydrate in addition to the glycerol as carbon source. The carbohydrate is selected in the group consisting of xylose, glucose, fructose and sucrose or combination thereof.

In a particular embodiment, glycerol is added to the medium in the form of glycerol composition comprising at least 50% of glycerol, preferably at least 85% of glycerol.

Advantageously, the glycerine used in the culture medium of the invention is industrial glycerine. "Industrial glycerine" means a glycerine product obtained from an industrial process without substantial purification. Industrial glycerine can also be designated as "raw glycerine". Industrial glycerine comprises more than 70% of glycerol, preferably more than 80%, water and impurities such as mineral salts and fatty acids. The maximum content of glycerol in industrial glycerine is generally 90%, more generally about 85%.

The method for the production of PDO and BA according to the present invention may thus be carried out by using glycerol provided by industrial glycerine comprising more than 70% of glycerol.

Industrial processes from which industrial glycerine is obtained are, inter alia, manufacturing methods where fats and oils, particularly fats and oils of plant origin or fats and oils of animal origin or used cooking oils, are processed into industrial products such as detergent or lubricants. In such manufacturing methods, industrial glycerine is considered as a by-product. In a particular embodiment, the industrial glycerine is a by-product from biodiesel production and comprises known impurities of glycerine obtained from biodiesel production, comprising about 80 to 85% of glycerol with salts, methanol, water and some other organic compounds such as fatty acids. Industrial glycerine obtained from biodiesel production may be further subjected to an acidification step to eliminate fatty acids. The man skilled in the art knows technology of acidification and is able to define the best conditions of acidification according to the glycerine used.

The method for the production of PDO and BA according to the present invention may thus be carried out by using industrial glycerine which is a by-product of biodiesel production.

The concentration of glycerol used in the method of the invention is more than 90 $g \cdot L^{-1}$ of glycerol in the fed medium. In preferred embodiments, the concentration is comprised between 90 and 200 $g \cdot L^{-1}$ of glycerol, more particularly between 90 and 140 g/L of glycerol, preferably about 120 $g \cdot L^{-1}$ of glycerol and more preferably about 105 $g \cdot L^{-1}$ of glycerol contained into the glycerine solution.

Preferably, the culture medium is a synthetic medium without addition of organic nitrogen. The method for the production of PDO and BA, according to the present invention may thus be carried out by using a culture medium which is exempt of organic nitrogen, and preferably using a synthetic medium without addition of organic nitrogen, more preferably without yeast extract.

Such culture media are disclosed in the art, particularly in patent applications WO 2010/128070 and WO 2011/042434, which contents are incorporated herein by reference.

In a particular embodiment, the method for the production of PDO and BA according to the present invention comprises culturing said mutant strain *Clostridium acetobutylicum* as defined above with at least one strain of *Clostridium sporogenes* and/or at least one strain of *Clostridium sphenoides*, in an appropriate culture medium comprising at least glycerol as carbon source and recovering the PDO and/or the BA produced from the culture medium.

EXAMPLES

The present invention is further defined in the following examples. It should be understood that these examples, while indicating preferred embodiments of the invention, are given by way of illustration only. From above disclosure and these examples, the person skilled in the art can make various changes of the invention to adapt it to various uses and conditions without modifying the essential means of the invention.

Example 1: Identification of Mutations Present in One Clone Strayed from the Type 174P Population Clone Isolation Clone isolation was performed on agar plates starting from continuous culture of the population strain *Clostridium acetobutylicum* DG1 pSPD5 Type 174P which is a population overexpressing the 1.3-propanediol operon from *C. butyricum* and adapted for growth and production of PDO from a culture medium with a high concentration of industrial glycerine as described in patent application WO2012/062832A1. The synthetic medium used for isolation on agar plate contained per liter of deionized water: agar, 25 g; commercial glycerine, 30 g; $KH_2PO_4$, 0.5 g; $K_2HPO_4$, 0.5 g; $MgSO_4$, $7H_2O$, 0.2 g; $CoCl_2$ $6H_2O$, 0.01 g; acetic acid, 99.8%, 2.2 ml; $NH_4Cl$, 1.65 g; MOPS, 23.03 g, biotin, 0.16 mg; p-amino benzoic acid, 32 mg; $FeSO_4$, $7H_2O$, 0.028 g; resazurin, 1 mg and cysteine, 0.5 g. The pH of the medium was adjusted to 6.5 with $NH_4OH$ 6N.

Isolated clones were considered pure after three subsequent subcultures on agar plates. One of them, named clone PD0557Vc05 was then transferred into liquid synthetic medium. Subsequently, growing liquid culture was conserved on glycerine 20% at −80° C. until characterization.

DNA Isolation

Genomic DNA was extracted from 16 ml of continuous culture of the clone PD0557Vc05 using the Genomic DNA buffer set and Genomic tip 500/G kits from Qiagen (QIAGEN SA, COURTABOEUF, France). Bacterial samples were prepared according to protocol described in the QIAGEN Genomic DNA Handbook (Sample Preparation and Lysis Protocol for Bacteria), followed by Genomic-tip Protocol (Protocol for Isolation of Genomic DNA from Blood, Cultured Cells, Tissue, Yeast, or Bacteria)

Sequencing Analysis

Genome of the clone PD0557Vc05 was sequenced using the Genome Sequencer Illumina HiSeq technology. The sequencing project was performed by GATC (GATC Biotech AG, Jakob-Stadler-Platz 7, 78467 Konstanz, Germany) with sequence mode Illumina HiSeq sequencing, standard genomic library, read length 2×150 bp, run type: paired end, read length: 2×150 bp, sequenced reads 11,589,200, sequenced bases 3,476,760,000.

Bioinformatic Analysis

The bioinformatics analysis was performed by GATC Biotech AG using the GATC VARIANT ANALYSIS V1.2 workflow and reference database ASM876v1. Variant analysis was performed by GATC Biotech AG: SNP and InDel calling is done using GATK's Haplotype Caller [McKenna et al., 2010; De Pristo et al., 2011); variants detected are annotated based on their gene context using snpEff (Cingolani et al., 2012). SnpEff software is available for instance on the website http://snpeff.sourceforge.net. Several metrics, that are used to evaluate the quality of a variant, are annotated using GATK's VariantAnnotator module; customised filters are applied to the variants to 1 lter false positive variants using GATK's VariantFiltration module.

Validation of the Identified Mutations

To confirm the presence of identified mutations in PD0557Vc05, PCR reactions and Sanger sequencing were done on DNA for each gene or DNA region of interest, using PCR and Sanger sequencing oligonucleotides described in Table 1.

TABLE 1

Oligonucleotides sequences designed for PCR and Sanger sequencing of mutated genes identified in the sequencing analysis; CA C1321, CA C0028, CA C0770 and CA C2709 genes

| Gene name | Oligonucleotides for PCR reactions | Oligonucleotides for Sanger sequencing |
|---|---|---|
| CA_C1321 (glpK) | SEQ ID NO: 30 ggagcaacatgtgtatcaacaacc SEQ ID NO: 31 GCATCCAATAACACCTGCTCC | SEQ ID NO: 30 ggagcaacatgtgtatcaacaacc SEQ ID NO: 31 GCATCCAATAACACCTGCTCC SEQ ID NO: 32 ggcaaagtccatgtaaccg |
| CA_C0028 (hydA) | SEQ ID NO: 33 catgttctattgttactatggaagaggtagtag SEQ ID NO: 34 GCAGTTATTATAAATGCTGCTACTAGAGC | SEQ ID NO: 33 catgttctattgttactatggaagaggtagtag SEQ ID NO: 35 cgtgaggttgacctccaccatttatacatcc SEQ ID NO: 34 GCAGTTATTATAAATGCTGCTACTAGAGC SEQ ID NO: 36 GTGGACAATGTTCTAGAAGAG |
| CA_C0770 | SEQ ID NO: 37 atgcattatagtttagctg SEQ ID NO: 38 CGTATTTATGTTAACACAGG | SEQ ID NO: 39 CTGTGACAAATCCATTTATATG SEQ ID NO: 38 CGTATTTATGTTAACACAGG |
| CA_C2709 (etfA) | SEQ ID NO: 40 gaagttaaaggacagggagaag SEQ ID NO: 41 GCAAATGCCTGAGCAATTCC | SEQ ID NO: 40 gaagttaaaggacagggagaag SEQ ID NO: 41 GCAAATGCCTGAGCAATTCC |

Based on both Illumina and Sanger sequencing analysis performed on PD0557Vc05, several mutations were identified as described in table 2.

plasmids obtained were transformed into *E. coli* strain BL21(DE3) star to purify each mutated protein and perform biochemical experiments.

TABLE 2

Mutations identified in PD0557Vc05 clone. Genes and corresponding protein sequences are presented with their respective SEQ ID NO.

| Protein names | Gene name | Uniprot ref | Protein sequence | DNA sequence | Protein sequence modification | Protein sequence | DNA sequence |
|---|---|---|---|---|---|---|---|
| Glycerol kinase (EC 2.7.1.30) (ATP:glycerol 3-phosphotransferase) (Glycerokinase) (GK) | glpK CA_C1321 | Q97JG4 | SEQ ID NO: 1 | SEQ ID NO: 2 | H22Y A347T V466M | SEQ ID NO: 13 | SEQ ID NO: 14 |
| Hydrogene dehydrogenase | hydA CA_C0028 | Q7D472 | SEQ ID NO: 15 | SEQ ID NO: 16 | I210* (stop codon) | SEQ ID NO: 17 | SEQ ID NO: 18 |
| Glycerol uptake facilitator protein, permease | CA_C0770 | Q97KZ6 | SEQ ID NO: 19 | SEQ ID NO: 20 | M13I | SEQ ID NO: 21 | SEQ ID NO: 22 |
| Electron transfer flavoprotein subunit alpha (Alpha-ETF) (Electron transfer flavoprotein large subunit) (ETFLS) | etfA CA_C2709 | P52039 | SEQ ID NO: 23 | SEQ ID NO: 24 | I105V | SEQ ID NO: 25 | SEQ ID NO: 26 |

Example 2: Characterization of the Mutations Identified in Genes glpK and hydA

A. Characterisation of Proteins Glycerol Kinase Wild Type (GlpK) and Mutants (GlpK*)

Three different point mutations were identified in glpK gene in the clone PD0557Vc05 leading to the mutant protein GlpK* with H22Y, A347T and V466M (table 2 above). In order to better characterize the effect of the mutations, we tested them individually or in combination. Therefore, the alleles coding for the mutated glycerol kinase were cloned into the expression plasmid pPAL7 (Biorad®) and the

TABLE 3 strains constructed and used for kinetic parameters determination of glycerol kinase mutants from PD0557Vc05

| Strain Number | Name | Uniprot Ref | protein sequence | gene sequence |
|---|---|---|---|---|
| 1 | GlpK wt | Q97JG4 | SEQ ID NO: 1 | SEQ ID NO: 2 |
| 2 | GlpK*(H22Y/A347T/V466M) | — | SEQ ID NO: 13 | SEQ ID NO: 14 |
| 3 | GlpK*(H22Y) | — | SEQ ID NO: 5 | SEQ ID NO: 6 |
| 4 | GlpK*(A347T) | — | SEQ ID NO: 3 | SEQ ID NO: 4 |
| 5 | GlpK*(V466M) | — | SEQ ID NO: 7 | SEQ ID NO: 8 |

TABLE 3-continued strains constructed and used for kinetic parameters determination of glycerol kinase mutants from PD0557Vc05

| Strain Number | Name | Uniprot Ref | protein sequence | gene sequence |
|---|---|---|---|---|
| 6 | GlpK*(H22Y/A347T) | — | SEQ ID NO: 9 | SEQ ID NO: 10 |
| 7 | GlpK*(A347T/V466M) | — | SEQ ID NO: 11 | SEQ ID NO: 12 |

Overproduction of the Proteins

Cultures of the seven strains 1 to 7 for the overproduction of the proteins were realized in a 2 L Erlenmeyer flask, using LB broth (Bertani, 1951) that was supplemented with 5 g/L glucose and 100 mg/L of ampicillin. An overnight culture was used to inoculate a 500 mL culture to an $OD_{600\ nm}$ of about 0.15. The culture was first kept on a shaker at 37° C. and 200 rpm until $OD_{600\ nm}$ was about 0.5 and then the culture was moved on a second shaker at 25° C. and 200 rpm until $OD_{600\ nm}$ was 0.6-0.8 (about one hour), before induction with 500 μM IPTG. The culture was kept at 25° C. and 200 rpm until $OD_{600\ nm}$ was around 4, and then it was stopped. Cells were centrifuged at 7000 rpm, 5 minutes at 4° C., and then stored at −20° C. This protocol was the same for strains 1 to 7.

Purification of the Proteins

Step 1: Preparation of Cell-Free Extracts.

For each strain, about 250 mg of *E. coli* biomass was suspended in 40 ml of 100 mM potassium phosphate pH 7.6, and a protease inhibitor cocktail. The cells suspension (15 ml per conical tube) was sonicated on ice (Bandelin sonoplus, 70 w) in a 50 ml conical tube during 8 cycles of 30 sec with 30 sec intervals. After sonication, cells were incubated for 30 min at room temperature with 5 mM $MgCl_2$ and 1 UI/ml of DNaseI. Cells debris were removed by centrifugation at 12000 g for 30 min at 4° C.

Step 2: Affinity Purification

The proteins were purified from the crude cell-extract by affinity on a Profinity column (BIORAD, Bio-Scale Mini Profinity exact cartridge 5 ml) according to the protocol recommended by the manufacturer. The crude extract was loaded on a 5 ml Profinity exact cartridge equilibrated with 100 mM potassium phosphate pH 7.6. The column was washed with 10 column volumes of the same buffer and incubated 45 min with 100 mM potassium phosphate pH 7.6, 100 mM fluoride at room temperature. The protein was eluted from the column with 2 column volumes of 100 mM potassium phosphate pH 7.6. The tag remained tightly bound to the resin and the purified protein was released. The fractions containing the protein were pooled, concentrated. Protein concentration was measured using the Bradford protein assay.

Determination of kinetic parameters of GlpK wild type and mutants Glycerol kinase activity (GLPK) that catalyses the following reaction: Glycerol+ATP=>Glycerol-3-Phosphate+ADP, was determined by measuring the ADP appearance by enzymatic coupling to NADH oxidation. The reaction mixture (1 mL) containing 50 mM Sodium bicarbonate pH 9, 2 mM ATP, 2 mM phosphoenolpyruvate, 0.2 mM NADH, 5 mM $MgCl_2$, 5 Units pyruvate kinase, 5 units lactate dehydrogenase was incubated for 5 min at 30° C. Then, 0.01-50 mM glycerol was added to start the reaction. The substrate glycerol was omitted from the blank. The oxidation of NADH was monitored at 30° C. by absorbance at 340 nm on a spectrophotometer ($\lambda_{340}$=6290 $M^{-1}$ $cm^{-1}$).

One unit of enzyme activity was defined as the amount of enzyme catalyzing the decrease of 1 μmol of NADH per min. Kinetic parameters were determined with Sigmaplot by fitting to the Michaelis-Menten equation. The specific activity and kinetic parameters of the purified enzymes towards glycerol are provided in Table 4.

TABLE 4 catalytic performances (Specific activity and Kinetic) of the wild type and GlpK mutants towards glycerol

| Catalytic performance on glycerol | GlpK wt | GlpK* A347T | GlpK* H22Y | GlpK* V466M | GlpK* (H22Y/A347T) | GlpK* (A347T/V466M) | GlpK* (H22Y/A347T/V466M) |
|---|---|---|---|---|---|---|---|
| Km (mM) | 0.054 ± 0.001 | 0.26 ± 0.031 | 0.070 ± 0.004 | 0.058 ± 0.003 | 0.62 ± 0.05 | 0.48 ± 0.048 | 0.039 ± 0.002 |
| Vm (nmol/min/mg) | 87734 ± 499 | 6977 ± 155 | 91725 ± 1186 | 60399 ± 537 | 9784 ± 195 | 6267 ± 175 | 1404 ± 13 |
| Kcat (min−1) | 4933 ± 28 | 392.3 ± 8.7 | 5158 ± 67 | 3396 ± 30 | 545 ± 11 | 352.4 ± 9.8 | 79.0 ± 0.7 |
| Kcat/km (mM−1s−1) | 1520 ± 53 | 24.9 ± 3.5 | 1229 ± 93 | 973 ± 52 | 14.7 ± 1.5 | 12.31 ± 1.6 | 33.9 ± 2.3 |

Each simple mutation decreases either the specific activity (A347T and V466M) or the affinity (A347T) towards the substrate glycerol. This conclusion is also true for the double mutants, which have reduced catalytic activity and affinity (H22Y/A347T and V466M/A347T).

The triple mutant GlpK* combining all the mutations (A347T/V466M/H22Y) shows a strong drop of the catalytic efficiency with a value of 33.9 $mM^{-1}s^{-1}$ compared to 1520 $mM^{-1}s^{-1}$ for the wild type protein.

The conclusion is that whatever the mutation or the combination of them, the catalytic activity of glycerol kinase is reduced more or less drastically. Therefore, the strain PD0557Vc05 has a reduced GlpK catalytic activity.

B. Characterization of the HydA Mutation

The more relevant mutation identified in the hydA gene lead to the integration of a stop codon at the amino acid position 210 as disclosed in the HydA protein alignment below:

HydA Protein Alignment: CA_C0028: HydA Wild-Type Protein and CA_C0028*(12107 Truncated HydA*(1210*)
CA_C0028 (161)
STCSIQFIKKDGQRAVGTVDDVCLDDSTCLLCGQ-CVIACPVAALKEKSHI
CA_C0028*(12101 (161)
STCSIQFIKKDGQRAVGTVDDVCLDDSTCLLCGQ-CVIACPVAALKKNPI—

In order to characterize the phenotype of the mutation, we measured the Hydrogen and Carbone dioxide production of a fermentation of the PD0557Vc05 clone during a continuous culture (Table 5). Fermentation gas samples were taken in Supel™-Inert Multi-Layer bags and analyzed by Quad-Lab laboratory. $H_2$ and $CO_2$ were quantified by μGC/μTCD in accordance with NFX 20-303.

TABLE 5

Hydrogen production by PD0557Vc05 in continuous culture.
Limit of quantification about 0.0005%; Error: 15%
Gaz reactor analysis

| Sample | $H_2$ (v/v %) | $CO_2$ (v/v %) |
|---|---|---|
| PD0557Vc05 | 0.0520 | 98.3028 |

These data show that the clone PD0557Vc05 does not produce hydrogen anymore but exclusively carbon dioxide. This confirms the absence of HydA activity.

This result has been validated by proteomic analysis performed on samples (cell extracts) of cultures of the clone. The HydA protein is not detected at all.

In conclusion, the clone PD0557Vc05 has no hydrogenase activity anymore.

Example 3: Effect of GlpK* and HydA Truncation on the PDO and BA Production by Two Producer Strains; C. acetobutylicum DG1 pSPD5 and PD0001VE05c08

In order to confirm the effect of the mutations identified in clone PD0557Vc05 on the production of PDO/BA (see Example 2), we introduced the glpK* and hydA* alleles, alone or in combination into two producer strains that are not modify on these genes. The two recipient strains chosen for the genetic modifications were:

DG1 pSPD5: C. acetobutylicum strain DG1 pSPD5 described in publication Gonzalez-Pajuelo et al., 2006
PD0001VE05c08: C. acetobutylicum strain DG1 pSPD5 isolated clone and adapted on high concentrations of glycerine as described in patent application WO2012/062832

Mutations in genes glpK* (triple mutant) and hydA* identified in strain PD0557Vc05 described above were introduced into the DG1 pSPD5 strain, giving rise to strains 8, 9 and 10 or in PD0001VE05c08 giving rise to strains 11, 12 and 13.

Strains 8 to 10 were cultivated in continuous culture conditions described in Gonzalez-Pajuelo et al., 2006, and strains 11 to 13 were cultivated as described in patent application WO2012/062832.

TABLE 6

Level of performances improvement of the C. acetobutylicum DG1 pSPD5 and PD0001VE05c08 strains carrying glpk* and/or hydA* mutations.
Q 1,3 PDO/BA corresponds to PDO/ABH volumetric productivity

| Strain | Genetic modification | Q 1,3 PDO improvement (%) | Q BA improvement (%) |
|---|---|---|---|
| Reference DG1 pSPD5 | — | — | — |
| 8 | glpK*(H22Y/A347T/V466M) hydA wt | +5% | +2% |
| 9 | glpK wt hydA*(1210*) | +3% | +4% |

TABLE 6-continued

Level of performances improvement of the C. acetobutylicum DG1 pSPD5 and PD0001VE05c08 strains carrying glpk* and/or hydA* mutations.
Q 1,3 PDO/BA corresponds to PDO/ABH volumetric productivity

| Strain | Genetic modification | Q 1,3 PDO improvement (%) | Q BA improvement (%) |
|---|---|---|---|
| 10 | glpK*(H22Y/A347T/V466M) hydA*(1210*) | +7% | +6% |
| Reference PD0001VE05c08 | — | — | — |
| 11 | glpK*(H22Y/A347T/V466M) hydA wt | +7% | +2% |
| 12 | glpK wt hydA*(1210*) | +4% | +6% |
| 13 | glpK*(H22Y/A347T/V466M) hydA*(1210*) | +9% | +7% |

Upon mutations of glpk and hydA genes leading respectively to the decrease of the glycerol kinase activity with GlpK* (H22Y/A347T/V466M) and to the suppression of the hydrogenase activity with HydA* (1210*), productivities of both PDO and BA are improved.

Example 4: Performances of PD0557Vc05 in a Continuous Culture with High Concentrations of Raw Glycerine Bacterial Strains:
PD0001VE05c08: C. acetobutylicum strain DG1 pSPD5 isolated clone and adapted on high concentrations of glycerine as described in patent application WO2012/062832
PD0557Vc05: C. acetobutylicum strain DG1 pSPD5 isolated clone from a continuous culture of C. acetobutylicum strain DG1 pSPD5 Type 174P on high concentrations of raw industrial glycerine as described in patent application WO2012/062832A1.

Culture Media:
The synthetic medium used for clostridia batch cultivations contained per liter of tap water: glycerol, 30 g; $KH_2PO_4$, 0.5 g; $K_2HPO_4$, 0.5 g; $MgSO_4$, $7H_2O$, 0.2 g; $CoCl_2$ $6H_2O$, 0.01 g; $H_2SO_4$, 0.1 ml; $NH_4Cl$, 1.5 g; biotin, 0.16 mg; p-amino benzoic acid, 32 mg and $FeSO_4$, $7H_2O$, 0.028 g. The pH of the medium was adjusted to 6.3 with $NH_4OH$ 3N. Commercial glycerol purchased from SDS Carlo_Erba (purity 99%) was used for batch cultivation. The feed medium for continuous cultures contained per liter of tap water: glycerol from raw glycerine, 105 g; $KH_2PO_4$, 0.45 g; $K_2HPO_4$, 0.45 g; $MgSO_4$, $7H_2O$, 0.2 g; $CoCl_2$ $6H_2O$, 0.013 g; biotin, 0.08 mg; p-amino benzoic acid, 16 mg; $FeSO_4$, $7H_2O$, 0.04 g; anti-foam, 0.05 ml; $ZnSO_4$, $7H_2O$, 8 mg; $CuCl_2$, $2H_2O$, 4 mg; $MnSO_4$, $H_2O$, 20 mg. Medium pH was adjusted between 3,5 and 4 with $H_2SO_4$ 96%. Raw glycerine, from the transesterification process for biodiesel, was provided by different providers (Avril, Carotech Berhad) and had purity comprised between 80 and 86% (w/w). These glycerines were blended and pretreated by acidification.

Experimental Set-Up:
Continuous cultures were performed in a 5 L bioreactor Tryton (Pierre Guerin, France) with a working volume of 2000 mL. The culture volume was kept constant at 2000 mL by automatic regulation of the culture level. Cultures were stirred at 200 RPM, the temperature was set to 35° C. and pH maintained constant at 6.5 by automatic addition of $NH_4OH$ 5.5 N. To create anaerobic conditions, the sterilized medium in the vessel was flushed with sterile O2-free nitrogen for one hour at 60° C. and flushed again until 35° C. was attained (flushing during 2 hours). The bioreactor gas outlet was protected from oxygen by a pyrogallol arrangement (Vasconcelos et al., 1994). After sterilization the feed medium was also flushed with sterile $O_2$-free nitrogen until room temperature was attained and maintained under nitrogen to avoid $O_2$ entry.

Batch and Continuous Cultures Process:

A culture growing in a 100 mL Penicillin flask on synthetic medium (the same as described above for batch culture but with addition of acetic acid, 2.2 g·$L^{-1}$ and MOPS, 23.03 g·$L^{-1}$) taken at the end of exponential growth phase was used as inoculum (5% v/v).

Cultures were first grown batchwise. At the early exponential growth phase we performed a pulse of glycerol from raw glycerine: For the pulse, synthetic medium (the same as described for feed culture) with 105 g·$L^{-1}$ of glycerol from raw glycerine was added at a static flow rate during 3 hours (i.e. an addition of 18 g·$L^{-1}$ of glycerol). Then the growth continued batchwise and before the end of the exponential growth phase the continuous feeding started with a dilution rate of 0.035 $h^{-1}$. The feed medium contains 105 g·$L^{-1}$ of glycerol from raw glycerine. 6-13 days after inoculation of the bioreactor and after 4 residence times (RT) the dilution rate was increased from 0.035 $h^{-1}$ to 0.070 $h^{-1}$ in five days. After that, stabilization of the culture was followed by PDO production and glycerol consumption using the HPLC protocol described below. Particularly we waited until the concentration of residual glycerine was as low as possible.

The overall performances of PD0557Vc05 are presented in table 7 below and compared with performances of PD0001VE05c08 obtained with culture media, batch and continuous process described in B60. These process conditions start at a dilution rate of 0.025 $h^{-1}$ and reached only a dilution rate of 0.06 $h^{-1}$. PD0001VE05c08 washout with process conditions described in this example and applied for the mutated strain PD0557Vc05 with higher dilution rate (start dilution rate at 0.035 $h^{-1}$ and reached a dilution rate at 0.07 $h^{-1}$).

Analytical Procedures:

Cell concentration was measured turbidimetrically at 620 nm and correlated with cell dry weight determined directly. Glycerol, 1,3-propanediol, ethanol, lactate, acetic and butyric acids concentrations were determined by HPLC analysis. Separation was performed on a Biorad Aminex HPX-87H column and detection was achieved by refractive index.

Operating conditions were as follows: mobile phase sulphuric acid 0.5 mM; flow rate 0.5 ml/min, temperature, 25° C.

TABLE 7

Performances of the *C. acetobutylicum* PD0001VE05c08 and PD0557Vc05 isolated clones grown in continuous culture (mean data from 2 chemostats). The feed medium contained 105 g · $L^{-1}$ of glycerol from raw glycerine, dilution rate was 0.025 $h^{-1}$ to 0.06 $h^{-1}$ for PD0001VE05c08 and 0.035 h-1 to 0.07 h-1 for PD0557Vc05. Values correspond to the average of samples analyzed after culture stabilization at the maximum dilution rate obtained.

| | PDO/BA Production performances for PD0001VE05c08 | PDO/BA Production performances for PD0557Vc05 |
|---|---|---|
| Feed glycerine (g · $l^{-1}$) | 104 | 105 |
| 1,3-propanediol (g · $l^{-1}$) | 50.4 | 49.2 |
| Butyric acid (g · $l^{-1}$) | 11.4 | 10.8 |

TABLE 7-continued

Performances of the *C. acetobutylicum* PD0001VE05c08 and PD0557Vc05 isolated clones grown in continuous culture (mean data from 2 chemostats). The feed medium contained 105 g · $L^{-1}$ of glycerol from raw glycerine, dilution rate was 0.025 $h^{-1}$ to 0.06 $h^{-1}$ for PD0001VE05c08 and 0.035 h-1 to 0.07 h-1 for PD0557Vc05. Values correspond to the average of samples analyzed after culture stabilization at the maximum dilution rate obtained.

| | PDO/BA Production performances for PD0001VE05c08 | PDO/BA Production performances for PD0557Vc05 |
|---|---|---|
| Y1,3-PDO (g · $g^{-1}$) | 0.49 | 0.47 |
| Q1,3-PDO (q · $l^{-1}$ · $h^{-1}$) | 2.99 | 3.40 |
| Y1,3-BA (g · $g^{-1}$) | 0.11 | 0.11 |
| Q1,3-BA (q · $l^{-1}$ · $h^{-1}$) | 0.67 | 0.75 |
| Dilution rate ($h^{-1}$) | 0.059 | 0.068 |
| Residual glycerine (g · $l^{-1}$) | 3.6 | 4.4 |
| Biomass (g · $l^{-1}$) | 1.99 | 2.28 |
| Acetic acid (g · $l^{-1}$) | 2.29 | 1.85 |

Y1,3-PDO/BA: PDO/BA yield (g/g of glycerol engaged)
Q1,3 PDO/BA: PDO/BA volumetric productivity These results show that the clone PD0557Vc05 carrying mutations on glpK and hydA genes described and characterized in examples above produces PDO and BA with higher productivities than clone PD0001VE05c08. The gain is significant as it is above 10% more productivity for both products (data in bold).

An important fact mentioned above is that the strain PD0001VE05c08 was not able to reach the dilution rate of 0.07 $h^{-1}$ on the contrary of PD0557Vc05 strain, confirming the positive impact of the claimed mutations on the growth rate and PDO and BA productivity of bacteria.

Moreover, when culture conditions described in WO2012/062832 were applied to PD0557Vc05 strain, the performances of said strain were better than PD0001VE05c08 ones (data not shown).

Example 5: Performances of Microbial Consortium Comprising Strains PD0557Vc05, *C. sporogenes* and *C. sphenoides* in Continuous Culture with High Concentrations of Raw Glycerine In order to improve the production of PDO and BA with the new strain PD0557Vc05, we decided to recreate a consortium of bacteria that has previously shown improvement on such production (not disclosed data). The consortium was therefore reconstituted by addition to PD0557Vc05, of microorganisms' *C. sphenoides* and *C. sporogenes*. This new consortium named "PD0557Vc05 consortium" was created during the first days of a continuous culture as describe below in section "batch and continuous cultures process".

Culture Media:

The synthetic media used for clostridia batch cultivations contained per liter of tap water: glycerol, 30 g; $KH_2PO_4$, 0.5 g; $K_2HPO_4$, 0.5 g; $MgSO_4$, $7H_2O$, 0.2 g; $CoCl_2$ $6H_2O$, 0.01 g; $H_2SO_4$, 0.1 ml; $NH_4Cl$, 1.5 g; biotin, 0.16 mg; p-amino benzoic acid, 32 mg and $FeSO_4$, $7H_2O$, 0.028 g. The pH of the medium was adjusted to 6.3 with $NH_4OH$ 3N. Commercial glycerol purchased from SDS Carlo_Erba (purity 99%) was used for batch cultivation. The feed medium for continuous cultures contained per liter of tap water: glycerol from raw glycerine (purity comprised between 80 and 86% w:w), 105 g; $KH_2PO_4$, 0.45 g; $K_2HPO_4$, 0.45 g; $MgSO_4$, $7H_2O$, 0.2 g; $CoCl_2$ $6H_2O$, 0.013 g; biotin, 0.08 mg; p-amino benzoic acid, 16 mg; $FeSO_4$, $7H_2O$, 0.04 g; anti-foam, 0.05 ml; $CuCl_2$, $2H_2O$, 2 mg; $MnSO_4$, $H_2O$, 20 mg. Medium pH was adjusted between 3.5 and 4 with $H_2SO_4$ 96%. Glycerine was pretreated by acidification.

Experimental Set-Up:

Continuous cultures were performed in a 5 L bioreactor Tryton (Pierre Guerin, France) with a working volume of 2000 mL. The culture volume was kept constant at 2000 mL by automatic regulation of the culture level. Cultures were stirred at 200 RPM, the temperature was set to 35° C. and pH maintained constant at 6.5 by automatic addition of $NH_4OH$ 5.5 N. To create anaerobic conditions, the sterilized medium in the vessel was flushed with sterile 02-free nitrogen for one hour at 60° C. and flushed again until 35° C. was attained (flushing during 2 hours). The bioreactor gas outlet was protected from oxygen by a pyrogallol arrangement (Vasconcelos et al., 1994). After sterilization the feed medium was also flushed with sterile 02-free nitrogen until room temperature was attained and maintained under nitrogen to avoid 02 entry.

Batch and Continuous Cultures Process:

The PD0557Vc05 culture growing in a 100 mL Penicillin flask on synthetic medium (the same as described above for batch culture but with addition of acetic acid, 2.2 g·$L^{-1}$ and MOPS, 23.03 g·$L^{-1}$) taken at the end of exponential growth phase was used as inoculum (5% v/v).

Cultures were first grown batchwise. At the early exponential growth phase we performed a pulse of glycerol from raw glycerine. For the pulse, synthetic medium (the same as described for feed culture) with 105 g·$L^{-1}$ of glycerol from raw glycerine was added at a static flow rate during 3 hours (i.e. an addition of 18 g·$L^{-1}$ of glycerol). Then the growth continued batchwise and before the end of the exponential growth phase the continuous feeding started with a dilution rate of 0.035 $h^{-1}$. The feed medium contained 105 g·$L^{-1}$ of glycerol from raw glycerine. 8 days after inoculation of the bioreactor, microbial consortium of *C. sporogenes* and *C. sphenoides* was added to have respectively an optical density (620 nm) of 0.009 uOD and 0.317 uOD in the bioreactor. After culture stabilization, the dilution rate was increased from 0.035 $h^{-1}$ to 0.070 $h^{-1}$. After that, stabilization of the culture was followed by 1,3-propanediol production, butyric acid production and glycerol consumption using the HPLC protocol described below. Particularly we waited until the concentration of residual glycerine was as low as possible. The overall performances of PD0557Vc05 consortium are presented in Table 8 and compared with performances of PD0557Vc05 without *C. sporogenes* and *C. sphenoides*.

Analytical Procedures:

Cell concentration was measured turbidimetrically at 620 nm and correlated with cell dry weight determined directly. Glycerol, 1,3-propanediol, ethanol, lactate, acetic and butyric acids concentrations were determined by HPLC analysis. Separation was performed on a Biorad Aminex HPX-87H column and detection was achieved by refractive index. Operating conditions were as follows: mobile phase sulphuric acid 0.5 mM; flow rate 0.5 ml/min, temperature, 25° C.

TABLE 8

Performances of the *C. acetobutylicum* PD0557Vc05 and of the PD0557Vc05 consortium grown in continuous culture. The feed medium contained 105 g · $L^{-1}$ of glycerol from raw glycerine, dilution rate was 0.07 $h^{-1}$. Values correspond to the average of samples analyzed after culture stabilization at dilution rate of 0.07 $h^{-1}$.

| | PDO/BA Production performances for PD0557Vc05 | PDO/BA Production performances for PD0557Vc05 consortium |
|---|---|---|
| Feed glycerine (g · $l^{-1}$) | 105 | 105 |
| 1,3-propanediol (g · $l^{-1}$) | 49.2 | 51.4 |
| Butyric acid (g · $l^{-1}$) | 10.8 | 11.2 |
| Y1,3-PDO (g · $g^{-1}$) engaged | 0.47 | 0.49 |
| Q1,3 PDO (g · $l^{-1}$ · $h^{-1}$) | 3.40 | 3.51 |
| Y1,3-BA (g · $g^{-1}$) engaged | 0.11 | 0.11 |
| Q1,3 BA (g · $l^{-1}$ · $h^{-1}$) | 0.75 | 0.77 |
| Dilution rate ($h^{-1}$) | 0.068 | 0.066 |
| Residual glycerine (g · $l^{-1}$) | 4.4 | 2.4 |
| Biomass (g · $l^{-1}$) | 2.28 | 2.12 |
| Acetic acid (g · $l^{-1}$) | 1.85 | 2.44 |

Y1,3-PDO: PDO/BA yield (g/g of glycerol engaged)
Q1,3 PDO: PDO/BA volumetric productivity These results show that the PD0557Vc05 consortium has better production performances both on PDO and BA than the PD0557Vc05 strain (data in bold). Indeed, the PD0557Vc05 consortium shows higher PDO and BA titers, higher yield of PDO and less residual glycerine, which means a clear overall improvement of the technology.

Microbial Consortium Quantification

DNA Isolation

Genomic DNA was extracted from 1 mL of culture, homogenized and transferred to 2 mL tube with Glass Bead Tube Kit, 0.1 mm, using a Precellys®24 lyser/homogeniser (Bertin Technologies, Saint Quentin Yvelines, France). Precellys®24 settings were: 6500 rpm, 20 sec cycle duration, 5 sec delay time between cycles, for 2 total cycles. After Precellys extraction, the lysate was centrifuged at 10,000 g for 10 min and the supernatant used for total genomic extraction using the NucleoSpin® Gel and PCR Clean-up from Macherey (Macherey Nagel, Hoerdt, France)

PD0557Vc05 Consortium Quantification by Quantitative PCR

The recent advances in molecular techniques such as PCR technology enable rapid, specific, and sensitive detection and the identification of potential microorganisms in different type of environments as for instance in this patent application, culture broth from a fermentative production.

Absolute quantification in samples was determined by quantitative PCR (qPCR) using the Sso Advanced Universal SYBR Green Supermix (Bio-rad Mitry Mory, France). The qPCR was performed on a Bio-Rad C1000™ Thermal Cycler equipped with a CFX96™ Real-Time System (Bio-Rad Mitry Mory, France).

Reactions mixtures consisted of 1×Sso Advanced Universal SYBR Green Supermix (Bio-Rad Mitry Mory, France), 6 μL of each forward (F) and reverse (R) primers (1 μM), 2 μL of diluted sample (2 ng/μL from Nanodrop measure) and nuclease free water to reach a final volume of 20 μL. Amplification was achieved according to the following thermal cycling program: initial melting at 98° C. for 2 min. (1 cycle) followed by 40 cycles of melting at 98° C. for 10 sec, annealing of primers and elongation at 60° C. for 30 sec. (Melt Curve 65 to 95° C., increment 0.5° C. every 5 sec).

A standard curve was determined for each microorganism using Cq values of serial dilutions of genomic DNA at known concentrations. The Cq value for each well (standard curve and samples) was determined by the CFX Manager™ 3.1 software. The samples were plotted against the standard curve to determine abundance of nucleic acid. Absolute quantification were based on one gapC gene copy per cell for *C. acetobutylicum*, one cpn60 gene copy per cell for *C. sphenoides* and one tpi gene copy per cell for *C. sporogenes*. For the purposes of calculation, nucleic acid extractions were assumed to be perfect, because no measurement of extraction efficiency is available.

Abundance of each microorganism in samples was determined by quantitative PCR (qPCR) using the Sso Advanced Universal SYBR Green Supermix (Bio-rad Mitry Mory, France) on a Bio-Rad C1000™ Thermal Cycler equipped with a CFX96™ Real-Time System. The gapC gene based primers used to target *C. acetobutylicum* were gapC_F, 5'-TGCTGCTGTAAGTATCATC-3' (SEQ ID NO: 42) and gapC_R, 5'-GTTGGAACTGGAACTCTT-3' (SEQ ID NO: 43). The cpn60 gene based primers used to target *C. sphenoides* were cpn60_F, 5'-TTATATGTGCACCGATATG-3' (SEQ ID NO: 44) and cpn60_R, 5'-GAGAAGTCTTGCGCCGGAC-3' (SEQ ID NO: 45). The tpi gene based primers used to target *C. sporogenes* were tpi_F, 5'-CCAGCGGTATTAGAAGAA-3' (SEQ ID NO: 46) and tpi_R, 5'-GTCCTATAATTACATAATGAACTC-3' (SEQ ID NO: 47).

In the table below, are given percentages of representation of the different species present in the PD0557Vc05 consortium considering that the totality of the cells contained in the culture corresponds to 100%.

TABLE 9

PD0557Vc05 microbial consortium composition after culture stabilization at dilution rate of 0.070 h$^{-1}$.

| Sample | *C. acetobutylicum* | *C.sphenoïdes* | *C.sporogenes* |
|---|---|---|---|
| Established permanent state culture | 89.67%-94.79% | 1.42%-4.52% | 3.79%-6.67% |

NON PATENT REFERENCES

Bantscheff M, Schirle M, Sweetman G, Rick J, and Kuster B. (2007), Analytical and Bioanalytical Chemistry, vol. 389(4): 1017-1031.

Bertani G. (1951), J Bacteriol. 62: 293-300.

Burnette W N (1981). Analytical Biochemistry, 112(2): 195-203.

DePristo M A, Banks E, Poplin R, Garimella K V, Maguire J R, Hartl C, Philippakis A A, del Angel G, Rivas M A, Hanna M, McKenna A, Fennell T J, Kernytsky A M, Sivachenko A Y, Cibulskis K, Gabriel S B, Altshuler D, and Daly M J. (2011), Nat Genet, 43:491-498.

Engvall E and Perlman P (1981), Immunochemistry, 8: 871-874.

González-Pajuelo M, Meynial-Salles I, Mendes F, Andrade J C, Vasconcelos I, and Soucaille P. 2005. Metabolic Engineering, 7: 329-336.

González-Pajuelo M, Meynial-Salles I, Mendes F, Soucaille P. and Vasconcelos I. (2006). Applied and Environmental Microbiology, 72: 96-101.

McKenna A, Hanna M, Banks E, Sivachenko A, Cibulskis K, Kernytsky A, Garimella K, Altshuler D, Gabriel S, Daly M, and DePristo M A. (2010), Genome Research, 20(9):1297-1303.

Papanikolaou S, Ruiz-Sanchez P, Pariset B, Blanchard F and Fick M. (2000), Journal of Biotechnology, 77: 191-208.

Platts A, Wang L L, Coon M, Nguyen T, Wang L, Land S J, Lu X and Ruden D M. (2012), Fly, 6(2): 80-92

Vasconcelos I, Girbal L, Soucaille P., (1994), Journal of Bacteriology, 176(5): 1443-1450.

---

The invention claimed is:

1. A mutant strain of *Clostridium acetobutylicum* expressing dhaB1, dhaB2 and dhaT genes from *C. butyricum* and comprising attenuated glycerol kinase activity, wherein the glycerol kinase is encoded by gene glpK with SEQ ID NO: 2 comprising at least one of the following mutations:

a. a mutation leading to a mutated protein with SEQ ID NO: 3, b. a mutation leading to a mutated protein with SEQ ID NO: 5, c. a mutation leading to a mutated protein with SEQ ID NO: 7.

2. The mutant strain according to claim 1, comprising at least a mutated gene with SEQ ID NO: 4 leading to a mutated protein with SEQ ID NO: 3.

3. The mutant strain according to claim 1, further comprising attenuated hydrogen dehydrogenase activity.

4. The mutant strain according to claim 3, wherein the hydrogen dehydrogenase is encoded by gene hydA with SEQ ID NO: 16.

5. The mutant strain according to claim 4 comprising at least a mutated gene with SEQ ID NO: 18.

6. The mutant strain according to claim 1, further comprising enhanced glycerol uptake facilitator permease activity.

7. The mutant strain according to claim 6, wherein the glycerol uptake facilitator protein is encoded by gene glpF with SEQ ID NO: 20.

8. The mutant strain according to claim 7 comprising at least a mutated gene with SEQ ID NO: 22.

9. The mutant strain according to claim 1, further comprising attenuated electron transfer flavoprotein subunit alpha activity.

10. The mutant strain according to claim 9, wherein the electron transfer flavoprotein subunit alpha is encoded by gene etfA with SEQ ID NO: 24.

11. The mutant strain according to claim 10 comprising at least a mutated gene with SEQ ID NO: 26.

12. A consortium of *Clostridium* comprising the mutant strain according to claim 1.

13. The consortium of *Clostridium* according to claim 12 comprising the mutant strain of *Clostridium acetobutylicum* as defined in claim 1 and at least one strain of *Clostridium sporogenes* and/or at least one strain of *Clostridium sphenoides*.

14. A method for the production of 1,3-propanediol and butyric acid comprising culturing the mutant strain as defined in claim 1, in an appropriate culture medium comprising at least glycerol and recovering the produced 1,3-propanediol and/or the butyric acid from the culture medium.

15. The method for the production of 1,3-propanediol and butyric acid according to claim 14, wherein produced 1,3-propanediol and/or butyric acid is further purified.

16. The method for the production of 1,3-propanediol and butyric acid according to claim 14, wherein glycerol concentration in the culture medium is from 90 to 120 g/L.

17. The method for the production of 1,3-propanediol and butyric acid according to claim 14, wherein the culture medium is exempt of organic nitrogen.

18. A method for the production of 1,3-propanediol and butyric acid comprising culturing the consortium as defined in claim 12 in an appropriate culture medium comprising glycerol and recovering the produced 1,3-propanediol and/or the butyric acid from the culture medium.

19. The mutant strain of *Clostridium acetobutylicum* of claim 1, wherein the glycerol kinase is encoded by gene glpK with SEQ ID NO: 2 comprising at least one of:

a. a mutated gene with SEQ ID NO: 4, b. a mutated gene with SEQ ID NO: 6, c. a mutated gene with SEQ ID NO: 8.

* * * * *